(12) United States Patent
Moroi et al.

(10) Patent No.: US 8,188,307 B2
(45) Date of Patent: May 29, 2012

(54) METHOD FOR PRODUCING AN OPTICALLY ACTIVE TETRAHYDROQUINOLINE

(75) Inventors: Takashi Moroi, Hiratsuka (JP); Tsukasa Sotoguchi, Tokyo (JP); Kazuhiko Matsumura, Hiratsuka (JP); Motonobu Takenaka, Hiratsuka (JP); Wataru Kuriyama, Hiratsuka (JP); Toshiyuki Murayama, Iwata (JP); Hideki Nara, Hiratsuka (JP); Tohru Yokozawa, Hiratsuka (JP); Kenji Yagi, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 390 days.

(21) Appl. No.: 12/550,948

(22) Filed: Aug. 31, 2009

(65) Prior Publication Data

US 2010/0036149 A1   Feb. 11, 2010

Related U.S. Application Data

(62) Division of application No. 10/545,899, filed on Oct. 3, 2005, now Pat. No. 7,601,842.

(30) Foreign Application Priority Data

Feb. 18, 2003   (JP) .................................. 2003-040351

(51) Int. Cl.
    *C07C 227/16*   (2006.01)
(52) U.S. Cl. ........................... 560/43; 564/163; 564/167
(58) Field of Classification Search .................... None
    See application file for complete search history.

(56) References Cited

U.S. PATENT DOCUMENTS

| 2,785,165 | A  | 3/1957 | Schock et al. |
| 6,600,045 | B2 | 7/2003 | Damon et al. |
| 6,689,897 | B2 | 2/2004 | Damon et al. |
| 6,706,881 | B2 | 3/2004 | Damon et al. |

FOREIGN PATENT DOCUMENTS

| GB | 776121 | 11/2002 |
| JP | 54-119414 A | 9/1979 |
| JP | 10-231286 A | 9/1998 |
| WO | 02/088069 A2 | 11/2002 |
| WO | 02/088085 | 11/2002 |

OTHER PUBLICATIONS

Kazuo Achiwa and Tsunehiko Soga, Tetrahedron Letters, The International Organ for the rapid publication of preliminary communications in organic chemistry, Catalytic Asymmetric Synthesis of Optically Active β-Amino Acids [1], Mar. 1978, pp. 1119-1120, No. 13, Pergamon Press: Oxford New York Paris Frankfurt.
R. Noyori and M. Kitamura, Enantioselective Catalysis with Metal Complexes. An Overview, Department of Chemistry, Nagoya University, Chikusa, Nagoya 464, (Japan), Modern Synthetic Methods 1989, pp. 116-198, vol. 5, Springer-Verlag Berlin Heidelberg, 1989.
Japanese Office Action in counterpart Appln No. 2006-502671 (inventor: Moroi et el), issued on Apr. 26, 2010.
Y. Ukaji et al., "Asymmetric Addition of Reformatsky-Type Reagent to Imines Utilizing Diisopropyl Tartrate as a Chiral Auxiliary", Chemistry Letters, pp. 254-255, 2001.
William D. Lubell et al., "Enantioselective Synthesis of β-Amino Acids Based on BINAP-Ruthenium(II) Catalyzed Hydrogenation", Tetrahedron Asymmetry, vol. 2, No. 7, pp. 543-554, 1991.
H. Irving et al., "Some Bromine-substituted Derivatives of 8-Hydroxyquinoline", Journal of Chemical Society, pp. 290-295, Jan. 1957.
Patrick Y.S. Lam et al.,"N-Arylation of a-aminoesters with p-tolylboronic acid promoted by copper(II) acetate", Tetrahedron Letters, vol. 44, No. 8, pp. 1691-1694, 2003.
J. C. Adrian et al., "Multiple Component Reactions: An Efficient Nickel-Catalyzed Reformatsky-Type Reaction and its Application in the Parallel Synthesis of 13-Amino Carbonyl Libraries", Journal of Organic Chemistry, vol. 68, No. 6, pp. 2143-2150, 2003.
G. Bartoli et al., "Chemo- and Diastereoselective Reduction of f3-Enamino Esters: A Convenient Synthesis of Both cis- and trans-y-Amino Alcohols and 13-Amino Esters", Journal of Organic Chemistry, vol. 59, No. 18, pp. 5328-5335, 1994.
H. B. MacPhillamy et al., "The Alkaloids of Tabernanthe iboga. Part VI. The synthesis of the selenium dehydrogenation products from ibogamine", Journal of the American Chemical Society, vol. 80, pp. 2172-2178, 1958.
H. Beitz, "Ethyl 3-arylaminolevulinate" Z. Chem.,, vol. 7, No. 8, p. 308, 1967.

(Continued)

*Primary Examiner* — Brian J Davis
(74) *Attorney, Agent, or Firm* — Sughrue Mion, PLLC

(57) ABSTRACT

Disclosed is an industrially advantageous production method of optically active β-amino acid of formula (5a), which includes subjecting an enaminoester of formula (4a) to an asymmetric hydrogenation:

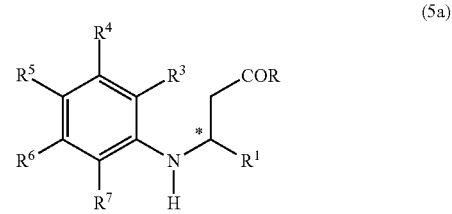

(5a)

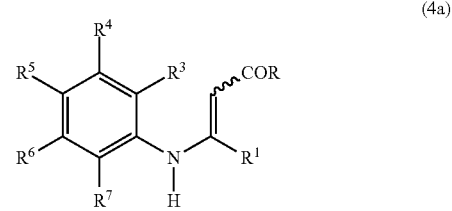

(4a)

wherein * shows an asymmetric carbon atom.

1 Claim, No Drawings

OTHER PUBLICATIONS

R. W. Carling et al., "2-Carboxytetrahydroquinolines. Conformational and Stereochemical Requirements for Antagonism of the Glycine Site on the NMDA Receptor", J. Med. Chem., vol. 35, pp. 1942-1953, 1992.

S. Kuo et al., "Synthesis and Cytotoxicity of 1,6,7,8-Substituted 2-(4'-Substituted phenyl)-4-quinolones and Related Compounds: Identification as Antimitotic Agents Interacting with Tubulin", J. Med. Chem., vol. 36, pp. 1146-1156, 1993.

K. Grohe et al., "Synthese von 4-Chinolon-3-carbonsauren", Liebigs Ann. Chemi., No. 1, pp. 29-37, 1987.

C. Cimarelli et al., "Stereoselective Reduction of Enantiopure p-Enamino Esters by Hydride: A Convenient Synthesis of both Enantiopure P-Amino Esters", J. Org. Chem., vol. 61, No. 16, pp. 5557-5563, 1996.

METHOD FOR PRODUCING AN OPTICALLY ACTIVE TETRAHYDROQUINOLINE

CROSS-REFERENCE TO RELATED APPLICATIONS

This is a Divisional of U.S. application Ser. No. 10/545,899 (issued as U.S. Pat. No. 7,601,842) filed Oct. 3, 2005, which claims benefit of Japanese Patent Application 2003-040351 filed Feb. 18, 2003. The entire disclosures of the prior applications, application Ser. No. 10/545,899 and Japanese Patent Application 2003-040351,. are hereby incorporated by reference.

TECHNICAL FIELD

The present invention relates to a method for producing optically active tetrahydroquinolines which are useful, for example, as intermediates for the synthesis of pharmaceuticals, agrochemicals, etc.

BACKGROUND ART

In recent years, tetrahydroquinolines are Widely used as pharmaceuticals, etc., and a variety of methods for producing them have been studied.

Production methods of tetrahydroquinolines via amino acid derivatives as intermediates have been disclosed (patent references 1 and 2, etc).

The patent references 1 and 2 disclose production methods of tetrahydroquinolines in which secondary amines obtained by the reactions of primary amines with aryl halogenides are used as the starting material. However, those methods require that the reaction conditions are selected so as not to bring about racemization in the process of introducing an alkyl or aryl group onto the amino group of optically active primary amines such as amino acids.

The non-patent reference 1 discloses a method for producing optically active amino acids in which the amino group is a secondary one by way of an asymmetric nucleophilic addition to the imines. However, for obtaining the desired amines, it is indispensable to use an excess amount of flammable diethylzinc, which has drawbacks in the workability, etc. of the reaction.

The non-patent reference 2 discloses a method for producing β-amino acid derivatives, in which enamines obtained by substituting the remaining hydrogen atom of a secondary amino group with an acetyl group, to an asymmetric hydrogenation. However, the method of the non-patent reference 2 has a drawback of requiring protection of the secondary amino group with a protecting group such as an acetyl group, etc., before subjecting the enamines to asymmetric hydrogenation, thus making two extra processes of introduction and removal of the protecting group indispensable.

Patent reference 1: WO02/088069
Patent reference 2: WO02/088085
Non-patent reference 1: Chemistry Letters, 254-255 (2001).
Non-patent reference 2: Tetrahedron Asymmetry, Vol. 2, No. 7, 543-554 (1991).

DISCLOSURE OF THE INVENTION

The present invention has been worked out in consideration of the problem mentioned above, and the aim of the present invention is to provide a method for producing optically active tetrahydroquinolines which does not require extra steps of introduction and removal of the protecting group, in its excellent workability and good asymmetric and chemical yields.

The present inventors have intensively studied on the method for producing optically active tetrahydroquinolines and found that the problem mentioned above can be solved by using the enaminoesters and optically active β-amino acid derivatives both of which are mentioned above as intermediates and have worked out the present invention.

Thus, the present invention is as follows:

(1) A method for producing an optically active tetrahydroquinoline of formula (1),

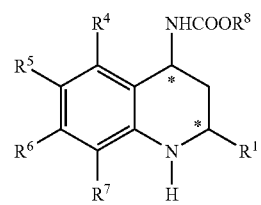

(1)

wherein $R^1$ is a hydrocarbon group, a substituted hydrocarbon group or $COOR^9$ ($R^9$ is a hydrocarbon group or a substituted hydrocarbon group); $R^4$ to $R^7$ are each independently a hydrogen atom, a hydrocarbon group, a halogen atom, a halogenated hydrocarbon group, a substituted hydrocarbon group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an acyl group, an acyloxy group, an alkoxycarbonyl group, an aryloxycarbonyl group, an aralkyloxycarbonyl group, an alkylenedioxy group, a hydroxy group, a nitro group, an amino group or a substituted amino group; $R^8$ is a hydrocarbon group or a substituted hydrocarbon group; * shows an asymmetric carbon atom; and, $R^4$ and $R^5$, $R^5$ and $R^6$, or $R^6$ and $R^7$, taken together, may form a fused ring, which method comprises the following steps:

1) a step of reacting a β-ketoester of formula (2), (2)

$$R^1 \underset{O}{\overset{}{\text{---}}} COOR^2$$

wherein $R^1$ is a hydrocarbon group, a substituted hydrocarbon group or $COOR^9$ (wherein $R^9$ is a hydrocarbon group or a substituted hydrocarbon group) and $R^2$ is a hydrocarbon group or a substituted hydrocarbon group, to react with an amine of formula (3), (3)

wherein $R^3$ to $R^7$ are each independently a hydrogen atom, a hydrocarbon group, a halogen atom, a halogenated hydrocarbon group, a substituted hydrocarbon group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an acyl group, an acyloxy group, an alkoxycarbonyl group, an aryloxycarbonyl group, an aralkyloxycarbonyl group, an alkylenedioxy group, a hydroxy group, a nitro group, an amino group or a substituted amino group; and, $R^3$ and $R^4$, $R^4$ and $R^5$, $R^5$ and $R^6$, or $R^6$ and $R^7$, taken together, may form a fused ring, with the proviso that either $R^3$ or $R^7$ is a hydrogen atom, to produce an enaminoester of formula (4),

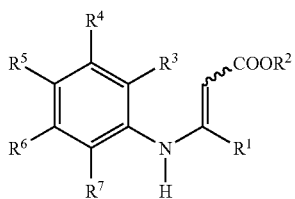

(4)

wherein $R^1$ to $R^7$ are each the same meaning as mentioned above;

2) a step of subjecting the enaminoester of formula (4) above obtained in 1) to an asymmetric hydrogenation to produce an optically active β-amino acid derivative of formula (5),

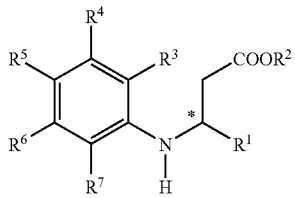

(5)

wherein * shows an asymmetric carbon atom and $R^1$ to $R^7$ are each the same meaning as mentioned above;

3) a step of amidating the optically active β-amino acid derivative of formula (5) above obtained in 2) above, to produce an amide of formula (6),

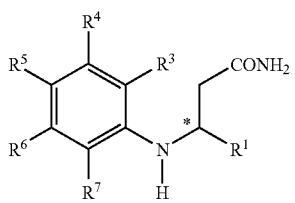

(6)

wherein, $R^1$, $R^3$ to $R^7$ and * have the same meanings as mentioned above;

4) a step of alkoxycarbonylating the amide of formula (6) above obtained in 3) above, to produce a compound of formula (7),

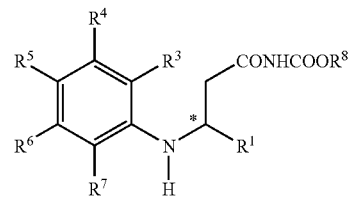

(7)

wherein $R^8$ is a hydrocarbon group or a substituted hydrocarbon group, and $R^1$, $R^3$ to $R^7$ and * have the same meanings as mentioned above; and 5) a step of subjecting the compound of formula (7) above obtained in 4) above to a cyclization to produce an optically active tetrahydroquinoline of formula (1) above.

(2) A method for producing an optically active tetrahydroquinoline of formula (1),

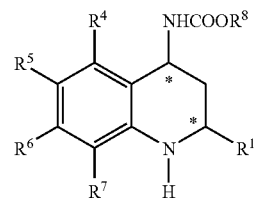

(1)

wherein, $R^1$ is a hydrocarbon group, a substituted hydrocarbon group or $COOR^9$ ($R^9$ is a hydrocarbon group or a substituted hydrocarbon group), $R^4$ to $R^7$ are each independently a hydrogen atom, a hydrocarbon group, a halogen atom, a halogenated hydrocarbon group, a substituted hydrocarbon group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an acyl group, an acyloxy group, an alkoxycarbonyl group, an aryloxycarbonyl group, an aralkyloxycarbonyl group, an alkylenedioxy group, a hydroxy group, a nitro group, an amino group or a substituted amino group; $R^8$ is a hydrocarbon group or a substituted hydrocarbon group; * shows an asymmetric carbon atom; and $R^4$ and $R^5$, $R^5$ and $R^6$, or $R^6$ and $R^7$, taken together, may form a fused ring, which method comprises the following steps:

1) a step of reacting a β-ketoester of formula (2),

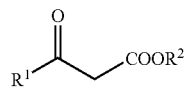

(2)

wherein $R^1$ is a hydrocarbon group, a substituted hydrocarbon group or $COOR^9$ ($R^9$ is a hydrocarbon group or a substituted hydrocarbon group, and $R^2$ is a hydrocarbon group or a substituted hydrocarbon group) with an amine of formula (3),

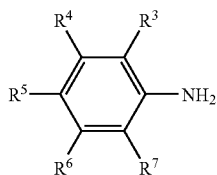

(3)

wherein $R^3$ to $R^7$ are each independently a hydrogen atom, a hydrocarbon group, a halogen atom, a halogenated hydrocarbon group, a substituted hydrocarbon group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an acyl group, an acyloxy group, an alkoxycarbonyl group, an aryloxycarbonyl group, an aralkyloxycarbonyl group, an alkylenedioxy group, a hydroxy group, a nitro group, an amino group or a substituted amino group; $R^3$ and $R^4$, $R^4$ and $R^5$, $R^5$ and $R^6$, or $R^6$ and $R^7$, taken together, may form a fused ring, with the proviso that either $R^3$ or $R^7$ is a hydrogen atom, to produce an enaminoester of formula (4),

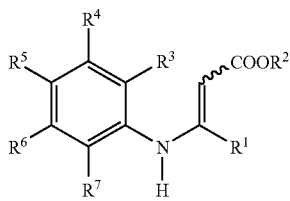

(4)

wherein, $R^1$ to $R^7$ have the same meanings as mentioned above;

2) a step of subjecting the enaminoester of formula (4) above obtained in 1) above to asymmetric hydrogenation to produce an optically active β-amino acid derivative of formula (5),

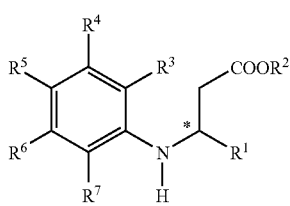

(5)

wherein * shows an asymmetric carbon atom and $R^1$ to $R^7$ have the same meanings as those mentioned above;

3) a step of reacting the optically active β-amino acid derivative obtained in 2) with a carbamate of formula (8),

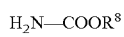

(8)

wherein $R^8$ is a hydrocarbon group or a substituted hydrocarbon group, to produce a compound of formula (7),

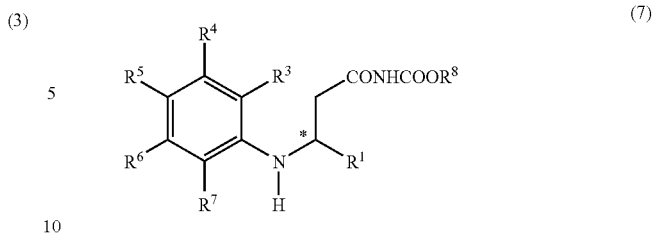

(7)

wherein $R^8$ is a hydrocarbon group or a substituted hydrocarbon group, and $R^1$, $R^3$ to $R^7$ and * have the same meanings as mentioned above; and 4) a step of subjecting the optically active compounds of formula (7) above obtained in 3) above to a cyclization to produce an optically active tetrahydroquinoline of formula (1) above.

(3) A method for producing an optically active tetrahydroquinoline of formula (1),

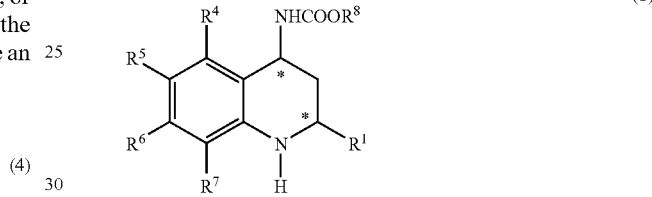

(1)

wherein, $R^1$ is a hydrocarbon group, a substituted hydrocarbon group or $COOR^9$ ($R^9$ is a hydrocarbon group or a substituted hydrocarbon group), $R^4$ to $R^7$ are each independently a hydrogen atom, a hydrocarbon group, a halogen atom, a halogenated hydrocarbon group, a substituted hydrocarbon group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an acyl group, an acyloxy group, an alkoxycarbonyl group, an aryloxycarbonyl group, an aralkyloxycarbonyl group, an alkylenedioxy group, a hydroxy group, a nitro group, an amino group or a substituted amino group; $R^8$ is a hydrocarbon group or a substituted hydrocarbon group; * shows an asymmetric carbon atom; and $R^4$ and $R^5$, $R^5$ and $R^6$, or $R^6$ and $R^7$, taken together, may form a fused ring, which method comprises the following steps:

1) a process of subjecting the enaminoester of formula (4),

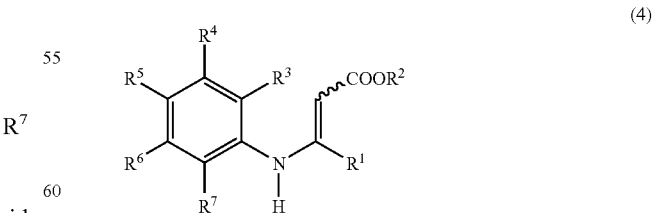

(4)

wherein $R^1$ is a hydrocarbon group, a substituted hydrocarbon group or $COOR^9$ ($R^9$ is a hydrocarbon group or a substituted hydrocarbon group), $R^2$ is a hydrocarbon group or a substituted hydrocarbon group; $R^3$ to $R^7$ are each independently a hydrogen atom, a hydrocarbon group, a halogen atom, a halogenated hydrocarbon group, a substituted hydrocarbon group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an acyl group, an acyloxy group, an alkoxycarbonyl group, an aryloxycarbonyl group, an aralkyloxycarbonyl group, an alkylenedioxy group, a hydroxy group, a nitro group, an amino group or a substituted amino group; $R^3$ and $R^4$, $R^4$ and $R^5$, $R^5$ and $R^6$, or $R^6$ and $R^7$, taken together, may form a fused ring, with the proviso that either $R^3$ or $R^7$ is a hydrogen atom, to an asymmetric hydrogenation to produce an optically active β-amino acid derivative of formula (5).

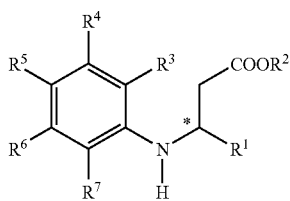

(5)

wherein * shows an asymmetric carbon atom, and $R^1$ to $R^7$ have the same meanings as mentioned above;

2) a step of amidating the optically active β-amino acid derivative of formula (5) above obtained in 1) above to produce an optically active amide of formula (6),

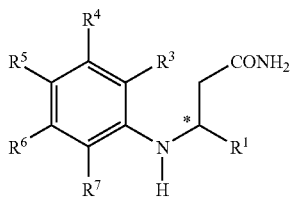

(6)

wherein $R^1$, $R^3$ to $R^7$ and * have the same meanings as mentioned above, 3) a step of alkoxycarbonylating the optically active amide of formula (6) above obtained in 2) above to produce a compound of formula (7),

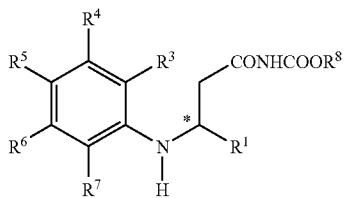

(7)

wherein $R^8$ is a hydrocarbon group or a substituted hydrocarbon group, and $R^1$, $R^3$ to $R^7$ and * have the same meanings as mentioned above; and 4) a step of subjecting the optically active compounds of formula (7) above obtained in 3) above to a cyclization to produce an optically active tetrahydroquinoline of formula (1) above.

(4) A method for producing an optically active tetrahydroquinoline of formula (1),

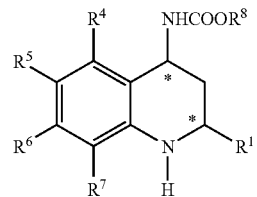

(1)

wherein $R^1$ is a hydrocarbon group, a substituted hydrocarbon group or $COOR^9$ ($R^9$ is a hydrocarbon group or a substituted hydrocarbon group). $R^4$ to $R^7$ are each independently a hydrogen atom, a hydrocarbon group, a halogen atom, a halogenated hydrocarbon group, a substituted hydrocarbon group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an acyl group, an acyloxy group, an alkoxycarbonyl group, an aryloxycarbonyl group, an aralkyloxycarbonyl group, an alkylenedioxy group, a hydroxy group, a nitro group, an amino group or a substituted amino group; $R^8$ is a hydrocarbon group; * shows an asymmetric carbon atom; and, $R^4$ and $R^5$, $R^5$ and $R^6$, or $R^6$ and $R^7$, taken together, may form a fused ring, which method comprises the following steps:

1) a step of subjecting an enaminoester of formula (4),

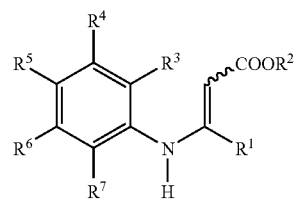

(4)

wherein $R^1$ is a hydrocarbon group, a substituted hydrocarbon group or $COOR^9$ ($R^9$ is a hydrocarbon group or a substituted hydrocarbon group); $R^2$ is a hydrocarbon group or a substituted hydrocarbon group; $R^3$ to $R^7$ are each independently a hydrogen atom, a hydrocarbon group, a halogen atom, a halogenated hydrocarbon group, a substituted hydrocarbon group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an acyl group, an acyloxy group, an alkoxycarbonyl group, an aryloxycarbonyl group, an aralkyloxycarbonyl group, an alkylenedioxy group, a hydroxy group, a nitro group, an amino group or a substituted amino group; and, $R^3$ and $R^4$, $R^4$ and $R^5$, $R^5$ and $R^6$, or $R^6$ and $R^7$, taken together, may form a fused ring, with the proviso that either $R^3$ or $R^7$ is a hydrogen atom, to an asymmetric hydrogenation to produce an optically active β-amino acid derivative of formula (5),

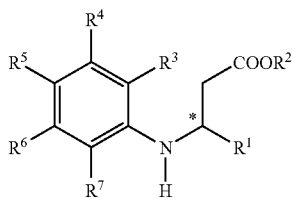

(5)

wherein * shows an asymmetric carbon atom, and $R^1$ to $R^7$ have the same meanings as described above;

2) a step of reacting the optically active β-amino acid derivative of formula (5) above obtained in 1) above with a carbamate of formula (8), $$H_2N-COOR^8 \quad (8)$$

wherein $R^8$ is a hydrocarbon group or a substituted hydrocarbon group, to produce a compound of formula (7),

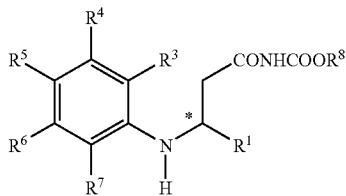

(7)

wherein $R^8$ is a hydrocarbon group or a substituted hydrocarbon group, and $R^1$, $R^3$ to $R^7$ and * have the same meanings as mentioned above;

3) a step of subjecting the optically active compound of formula (7) above obtained in 2) above to a cyclization to produce an optically active tetrahydroquinoline of the formula (1) mentioned above.

(5) A β-amino acid derivative of formula (15c),

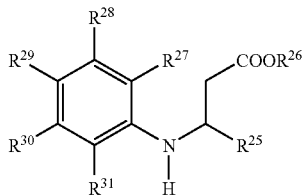

(15c)

wherein $R^{25}$ is a hydrocarbon group or $COOR^{32}$ ($R^{32}$ is a hydrocarbon group or a substituted hydrocarbon group); $R^{26}$ is a hydrocarbon group or a substituted hydrocarbon group; $R^{27}$ to $R^{31}$ are each independently a hydrogen atom, a hydrocarbon group, a halogen atom, a halogenated hydrocarbon group or an alkoxy group, with the proviso that i) either $R^{27}$ or $R^{31}$ is a hydrogen atom ii) at least one of $R^{27}$ to $R^{31}$ is a hydrocarbon group, a halogen atom, a halogenated hydrocarbon group or an alkoxy group, iii) when at least one of $R^{27}$ to $R^{31}$ is an alkoxy group, $R^{25}$ is a methyl group or an ethyl group, and iv) when at least one of $R^{27}$ to $R^{31}$ is a halogen atom or a methyl group, $R^{25}$ is a hydrocarbon group.

(6) A method for producing an optically active β-amino acid derivative of formula (5a),

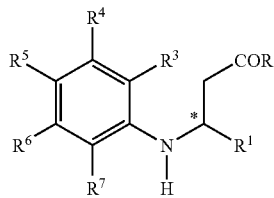

(5a)

wherein R is $OR^2$ ($R^2$ is a hydrocarbon group or a substituted hydrocarbon group) or an amino group, $R^1$ is a hydrocarbon group, a substituted hydrocarbon group or $COOR^9$ ($R^9$ is a hydrocarbon group or a substituted hydrocarbon group); $R^3$ to $R^7$ are each independently a hydrogen atom, a hydrocarbon group, a halogen atom, a halogenated hydrocarbon group, a substituted hydrocarbon group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an acyl group, an acyloxy group, an alkoxycarbonyl group, an aryloxycarbonyl group, an aralkyloxycarbonyl group, an alkylenedioxy group, a hydroxy group, a nitro group, an amino group or a substituted amino group; $R^3$ and $R^4$, $R^4$ and $R^5$, $R^5$ and $R^6$, or $R^6$ and $R^7$, taken together, may form a fused ring, with the proviso that either $R^3$ or $R^7$ is a hydrogen atom, which method comprises subjecting an enaminoester of formula (4a),

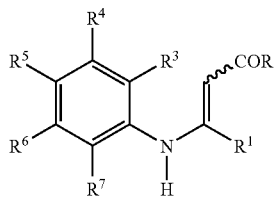

(4a)

wherein * shows an asymmetric carbon atom; and R, $R^1$ and $R^3$ to $R^7$ have the same meanings as mentioned above, to an asymmetric hydrogenation.

(7) An enaminoester of formula (9),

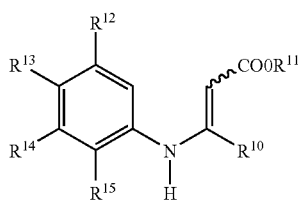

(9)

wherein $R^{10}$ is a hydrocarbon group or $COOR^{16}$ ($R^{16}$ is a hydrocarbon group or a substituted hydrocarbon group); $R^{11}$ is a hydrocarbon group or a substituted hydrocarbon group; $R^{12}$ to $R^{15}$ are each independently a hydrogen atom, a hydrocarbon group, an alkoxy group, a halogen atom or a halogenated hydrocarbon group, with the proviso that at least one of $R^{12}$ to $R^{15}$ is an alkoxy group, a halogen atom or a halogenated hydrocarbon group, and that when at least one of $R^{12}$ to $R^{15}$ is $CF_3$ or a bromine atom, $R^{10}$ is a hydrocarbon group except for a methyl group, and when at least one of $R^{12}$ to $R^{15}$ is a halogen atom, $R^{10}$ is a hydrocarbon group except for a methyl group.

(8) A method for producing a β-amino acid derivative of formula (22),

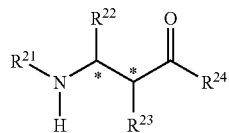
(22)

wherein $R^{21}$ is a hydrocarbon group; $R^{22}$ is a hydrogen atom, a hydrocarbon group, a substituted hydrocarbon group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted group, an alkoxycarbonyl group, an aryloxycarbonyl group, an aralkyloxycarbonyl group; $R^{23}$ is a hydrogen atom, a hydrocarbon group, a substituted hydrocarbon group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an acyloxy group, an alkyloxycarbonyl group, an aryloxycarbonyl group or an aralkyloxycarbonyl group; $R^{24}$ is a hydrocarbon group, an alkoxy group, a substituted alkoxy group, an aralkyloxy group, a substituted aralkyloxy group, an aryloxy group, a substituted aryloxy group, an amino group or a substituted amino group; and, $R^{22}$ and $R^{23}$, or $R^{23}$ and $R^{24}$, taken together, may form a ring, which method comprises allowing an enamino compound of formula (21),

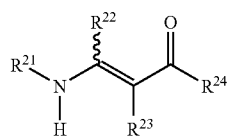
(21)

wherein * shows a asymmetric carbon atom, and $R^{21}$ to $R^{24}$ have the same meanings as mentioned above, to an asymmetric hydrogenation.

BEST MODE FOR CARRYING OUT THE INVENTION

The following is the description about the individual groups in formulae (1) to (8) above and other formulae.

Examples of the hydrocarbon group include, for example, an alkyl group, an alkenyl group, an alkynyl group, an aryl group and an aralkyl group.

The alkyl groups may be a straight, branched or cyclic one of, for example, 1 to 10 carbon atoms, and the specific examples thereof include groups such as methyl, ethyl, n-propyl, 2-propyl, n-butyl, 2-butyl, isobutyl, tert-butyl, n-pentyl, 2-pentyl, tert-pentyl, 2-methylbutyl, 3-methylbutyl, 2,2-dimethylpropyl, n-hexyl, 2-hexyl, 3-hexyl, 2-methylpentan-2-yl, 3-methylpentan-3-yl, 2-methylpentyl, 3-methylpentyl, 4-methylpentyl, 2-methylpentan-3-yl, heptyl, octyl, 2-ethylhexyl, nonyl, decyl, cyclopropyl, cyclobutyl, cyclopentyl, cyclohexyl, etc. Among them, alkyl groups of 1 to 6 carbon atoms are preferable.

The alkenyl groups may be a straight or branched one of, for example, 2 to 10 carbon atoms, and the specific examples thereof include groups such as ethenyl, propenyl, 1-butenyl, 2-butenyl, pentenyl, hexenyl, heptenyl, octenyl, nonenyl, decenyl, etc. Among them, alkenyl groups of 2 to 6 carbon atoms are preferable.

The alkynyl groups may be a straight or branched one of, for example, 2 to 10 carbon atoms, and the specific examples thereof include groups such as ethynyl, 1-propynyl, 2-propynyl, 1-butynyl, 3-butynyl, pentynyl, hexynyl, etc. Among them, alkynyl groups of 2 to 6 carbon atoms are preferable.

The aryl groups are those of 6 to 14 carbon atoms, and the specific examples thereof include groups such as phenyl, naphthyl, anthryl, biphenyl, etc.

The aralkyl group is the one which is formed by replacing at least one hydrogen atom of the alkyl groups mentioned above with an aryl group mentioned above. Thus, aralkyl groups of 7 to 15 carbon atoms are preferable. Specific examples of them include benzyl, 2-phenylethyl, 1-phenylpropyl, 3-naphthylpropyl, etc.

The halogen atoms include fluorine, chlorine, bromine, iodine atoms, etc.

The halogenated alkyl groups are those of 1 to 10 carbon atoms which are derived from the alkyl groups mentioned above by replacing at least one of their hydrogen atom(s) with halogen atom(s) (for example, fluorine, chlorine, bromine, iodine atoms, etc.). Specific examples of them include groups such as chloromethyl, bromomethyl, 2-chloroethyl, 3-bromopropyl, fluoromethyl, fluoroethyl, fluoropropyl, fluorobutyl, fluoropentyl, fluorohexyl, fluoroheptyl, fluorooctyl, fluorononyl, fluorodecyl, difluoromethyl, difluoroethyl, fluorocyclohexyl, trifluoromethyl, 2,2,2-trifluoroethyl, 3,3,3-trifluoropropyl, pentafluoroethyl, 3,3,4,4,4-pentafluorobutyl, perfluoro-n-propyl, perfluoroisopropyl, perfluoro-n-butyl, perfluoroisobutyl, perfluoro-tert-butyl, perfluoro-sec-butyl, perfluoro-n-pentyl, perfluoroisopentyl, perfluoro-tert-pentyl, perfluoro-n-hexyl, perfluoroisohexyl, perfluoroheptyl, perfluorooctyl, perfluorononyl, perfluorodecyl, 2-perfluorooctylethyl, perfluorocyclopropyl, perfluorocyclopentyl, perfluorocyclohexyl, etc.

Among these halogenated alkyl groups, those of 1 to 6 carbon atoms and perfluoroalkyl group are preferable and those of 1 to 3 carbon atoms are more preferable. Furthermore, fluorine-containing alkyl groups of 1 to 3 carbon atoms such as fluoromethyl, fluoroethyl, fluoropropyl, difluoromethyl, difluoroethyl, trifluoromethyl, 2,2,2-trifluoroethyl, 3,3,3-trifluoropropyl, pentafluoroethyl, perfluoro-n-propyl, perfluoroisopropyl, etc. are most preferable.

The acyl groups are a straight branched one of 1 to 18 carbon atoms derived from aliphatic or aromatic carboxylic acids, etc. Specific examples of such acyl groups include groups such as formyl, acetyl, propionyl, butyryl, pivaloyl, pentanoyl, hexanoyl, lauroyl, stearoyl, benzoyl, etc.

The aliphatic heterocyclic groups are for example, 5- to 8-membered, or more preferably, 5- to 6-membered monocyclic, polycyclic or fused-ring aliphatic heterocyclic groups which are composed of 2 to 14 carbon atoms, and, as heteroatoms, at least one, and more preferably 1 to 3 heteroatoms such as nitrogen, oxygen, sulfur atoms, etc. Specific examples of such aliphatic heterocyclic groups include, for example, 2-oxo-pyrrolidinyl, piperidino, piperazinyl, morpholino, morpholinyl, tetrahydrofuryl, tetrahydropyranyl, etc.

The aromatic heterocyclic groups are, for example, 5- to 8-membered, or more preferably, 5- to 6-membered monocyclic, polycyclic or fused-ring aromatic heterocyclic groups which are composed of 2 to 15 carbon atoms, and, as heteroatoms, at least one, and more preferably 1 to 3 heteroatoms such as nitrogen, oxygen, sulfur atoms, etc. Specific examples of such aromatic heterocyclic groups include, for example, furyl, thienyl, pyridyl, pyrimidyl, pyrazyl, pyridazyl, pyrazolyl, imidazolyl, oxazolyl, thiazolyl, benzofuryl, benzothienyl, quinolyl, isoquinolyl, quinoxalyl, phthalazyl, quinazolyl, naphthyridyl, cinnolyl, benzimidazolyl, benzoxazolyl, and benzothiazolyl.

The alkoxy groups may be straight, branched or cyclic alkoxy groups of, for example, 1 to 6 carbon atoms, and specific examples of such alkoxy groups include, for example, methoxy, ethoxy, n-propoxy, 2-propoxy, n-butoxy, 2-butoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, cyclohexyloxy, etc.

The aryloxy groups are those of, for example, 6 to 14 carbon atoms, and specific examples of such aryloxy groups include phenyloxy, naphthyloxy, anthryloxy, etc.

The aralkyloxy groups are those of, for example, 7 to 12 carbon atoms, and specific examples of such aralkyloxy groups include benzyloxy, 2-phenylethoxy, 1-phenylpropoxy, 2-phenylpropoxy, 3-phenylpropoxy, 1-phenylbutoxy, 2-phenylbutoxy, 3-phenylbutoxy, 4-phenylbutoxy, 1-phenylpentyloxy, 2-phenylpentyloxy, 3-phenylpentyloxy, 4-phenylpentyloxy, 5-phenylpentyloxy, 1-phenylhexyloxy, 2-phenylhexyloxy, 3-phenylhexyloxy, 4-phenylhexyloxy, 5-phenylhexyloxy, 6-phenylhexyloxy, etc.

The alkoxycarbonyl groups may be straight, branched or cyclic alkoxycarbonyl groups of, for example, 2 to 19 carbon atoms, and specific examples of such alkoxycarbonyl groups include methoxycarbonyl, ethoxycarbonyl, n-propoxycarbonyl, 2-propoxycarbonyl, n-butoxycarbonyl, tert-butoxycarbonyl, pentyloxycarbonyl, hexyloxycarbonyl, 2-ethylhexyloxycarbonyl, lauryloxycarbonyl, stearyloxycarbonyl, cyclohexyloxycarbonyl, etc.

The aryloxycarbonyl groups are those of, for example, 7 to 20 carbon atoms, and specific examples of such aryloxycarbonyl groups include phenoxycarbonyl, naphthyloxycarbonyl, etc.

The aralkyloxycarbonyl groups are those of, for example, 8 to 15 carbon atoms, and specific examples of such aralkyloxycarbonyl groups include benzyloxycarbonyl, phenylethoxycarbonyl, 9-fluorenylmethyloxycarbonyl, etc.

The acyloxy groups are straight or branched ones of, for example, 2 to 18 carbon atoms derived from carboxylic acids such as aliphatic carboxylic acids and aromatic carboxylic acids, and specific examples of such acyloxy groups include acetoxy, propionyloxy, butyryloxy, pivaloyloxy, pentanoyloxy, hexanoyloxy, lauryloxy, stearoyloxy, benzoyloxy, etc.

Examples of the substituted hydrocarbon groups include substituted alkyl groups, substituted alkenyl groups, substituted alkynyl groups, substituted aryl groups and substituted aralkyl groups.

The substituted alkyl groups include the alkyl groups as mentioned above, at least one of the hydrogen atoms of which are substituted with a substituent such as alkyl groups, alkoxy groups, halogen atoms, amino groups or substituted amino groups, etc., wherein the alkyl groups, the alkoxy groups and the halogen atoms are the same as those mentioned above, and the substituted amino groups are the same as those to be described below, and the alkyl groups substituted with halogen atoms, namely the halogenated alkyl groups are the same as those described above.

The substituents in the substituted alkenyl groups (for example, the substituted vinyl groups) and substituted alkynyl groups (for example, the substituted propargyl groups) can also be the same as those mentioned above.

The substituted aryl groups include the aryl groups as mentioned above, at least one of the hydrogen atoms of which are substituted with a substituent such as alkyl groups, halogenated hydrocarbon groups, alkoxy groups, halogen atoms, amino groups, substituted amino groups, etc., and also the aryl groups, two adjacent hydrogen atoms of which are replaced by substituents such as alkylenedioxy groups, etc., wherein the alkyl groups, the halogenated hydrocarbon groups, the alkoxy groups, the halogen atoms, and the substituted amino groups are the same as mentioned above, and the substituted amino groups are the same as described below. Specific examples of the aryl groups substituted with alkyl groups include a tolyl group and a xylyl group. The alkylenedioxy groups can be alkylenedioxy groups of 1 to 3 carbon atoms. Specific examples of the alkylenedioxy groups include methylenedioxy, ethylenedioxy, propylenedioxy, trimethylenedioxy, etc.

The substituted aralkyl groups include those mentioned above, at least one of the hydrogen atoms of which are substituted with a substituent such as alkyl groups, halogenated hydrocarbon groups, alkoxy groups, halogen atoms, amino groups, substituted amino groups, etc., and the aralkyl groups, two adjacent hydrogen atoms on the aryl group of which are replaced with substituents such as alkylenedioxy groups, etc., wherein the alkyl groups, the halogenated hydrocarbon groups, the alkoxy groups, the halogen atoms, and the substituted amino groups are the same as mentioned above, and the substituted amino groups are the same as described below.

The substituted aliphatic heterocyclic groups include those mentioned above, at least one of the hydrogen atoms of which is substituted with a substituent such as alkyl groups, halogenated hydrocarbon groups, alkoxy groups, halogen atoms, etc., wherein the alkyl groups, the halogenated hydrocarbon groups, the alkoxy groups and the halogen atoms are the same as mentioned above.

The substituted aromatic heterocyclic groups include those mentioned above, at least one of the hydrogen atoms of which are substituted with a substituent such as alkyl groups, halogenated hydrocarbon groups, alkoxy groups, halogen atoms, etc., wherein the alkyl groups, the halogenated hydrocarbon groups, the alkoxy groups, and the halogen atoms are the same as mentioned above.

The substituted alkoxy groups include those mentioned above, at least one of the hydrogen atoms of which are substituted with a substituent such as alkyl groups, halogenated hydrocarbon groups, alkoxy groups, halogen atoms, amino groups, substituted amino groups, etc., wherein the alkyl groups, the halogenated hydrocarbon groups, the alkoxy groups, and the halogen atoms and the substituted amino groups are the same as mentioned above and the substituted amino groups are the same as described below.

The substituted aryloxy groups include those mentioned above, at least one of the hydrogen atoms of which are substituted with a substituent such as alkyl groups, halogenated hydrocarbon groups, alkoxy groups, halogen atoms, amino groups and substituted amino groups, and the aryloxy groups, two adjacent hydrogen atoms on the aryl group of which are replaced by substituents such as an alkylenedioxy group, etc., wherein the alkyl groups, the halogenated hydrocarbon groups, the alkoxy groups, the halogen atoms, and the substituted amino groups and the alkylenedioxy groups are the same as mentioned above, and the substituted amino groups are the same as described below.

The substituted aralkyloxy groups include the same aralkyloxy groups as mentioned above, at least one of the hydrogen atoms of which are substituted with a substituent such as alkyl groups, halogenated hydrocarbon groups, alkoxy groups, halogen atoms, the amino groups and substituted amino groups, and aralkyloxy groups, two adjacent hydrogen atoms on the aryl group of which are replaced by substituents such as alkylenedioxy groups, etc., wherein the alkyl groups, the halogenated hydrocarbon groups, the alkoxy groups, the halogen atoms, the substituted amino groups and the alkylenedioxy groups are the same as those mentioned above, and the substituted amino groups are the same as the substituted amino groups described below.

The substituted amino groups include amino groups of which one or two hydrogen atoms are substituted with substituents such as protective groups, etc. Any protective groups can be used so long as they are used as amino protecting groups, and may be selected from those described in PROTECTIVE GROUPS IN ORGANIC SYNTHESIS Second Edition (JOHN WILEY & SONS, INC) as amino protecting groups. Specific examples of the amino protecting groups include an alkyl group, an aryl group, an aralkyl group, an acyl group, an alkoxycarbonyl group, an aryloxycarbonyl group, an aralkyloxycarbonyl group, etc., wherein the alkyl, aryl, aralkyl, acyl, alkoxycarbonyl, aryloxycarbonyl and aralkyloxycarbonyl groups are the same as those mentioned above.

Specific examples of the amino groups substituted with alkyl group(s), namely alkyl-substituted amino groups, include mono- or dialkylamino groups, such as N-methylamino, N,N-dimethylamino, N,N-diethylamino, N,N-diisopropylamino, N-cyclohexylamino, etc. Specific examples of the amino groups substituted with aryl group(s), namely aryl-substituted amino groups, include mono- or diarylamino groups, such as N-phenylamino, N,N-diphenylamino, N-naphthylamino, N-naphthyl-N-phenylamino, etc. Specific examples of the amino groups substituted with aralkyl group(s), namely aralkyl-substituted amino groups, include mono- or diaralkylamino groups, such as N-benzylamino, N,N-dibenzylamino, etc. Specific examples of the amino groups substituted with acyl group(s), namely acylamino groups, include formylamino, acetylamino, propionylamino, pivaloylamino, pentanoylamino, hexanoylamino, and benzoylamino, etc. Specific examples of the amino groups substituted with alkoxycarbonyl group(s), namely alkoxycarbonylamino groups, include methoxycarbonylamino, ethoxycarbonylamino, n-propoxycarbonylamino, n-butoxycarbonylamino, tert-butoxycarbonylamino, pentyloxycarbonylamino, hexyloxycarbonylamino, etc. Specific examples of the amino groups substituted with aryloxycarbonyl group(s), namely aryloxycarbonylamino groups, include amino groups, one of the hydrogen atoms of which is substituted with an aryloxycarbonyl group mentioned above, e.g., more specifically, phenoxycarbonylamino, and naphthyloxycarbonylamino groups. Specific examples of the amino groups substituted with an aralkyloxycarbonyl group, namely aralkyloxycarbonylamino groups, include benzyloxycarbonylamino group, etc.

Here, the groups preferable as $R^3$ to $R^7$ are hydrocarbon groups, halogen atoms or halogenated hydrocarbon groups, and at least one of $R^3$ to $R^7$ is a halogen atom or a halogenated hydrocarbon group, and either $R^3$ or $R^7$ is a hydrogen atom.

Specific examples of β-ketoesters (hereinafter called as β-ketoesters (2)) of formula (2) include the following compounds:

β-ketoesters (2) such as

methyl 3-oxopentanoate

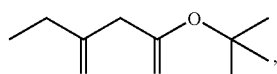

t-butyl 3-oxopentanoate

ethyl 3-oxopentanoate

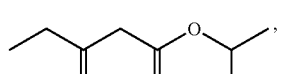

isopropyl 3-oxopentanoate

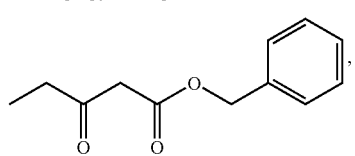

benzyl 3-oxopentanoate

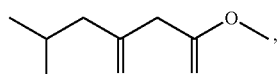

methyl 5-methyl-3-oxohexanoate

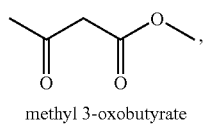

methyl 3-oxobutyrate

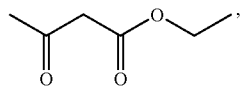

ethyl 3-oxobutyrate

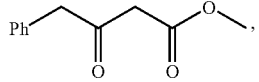

methyl 3-oxo-4-phenylbutyrate

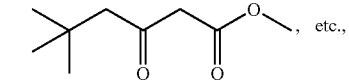

methyl 5,5-dimethyl-3-oxohexanoate

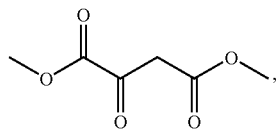

dimethyl 2-oxosuccinate

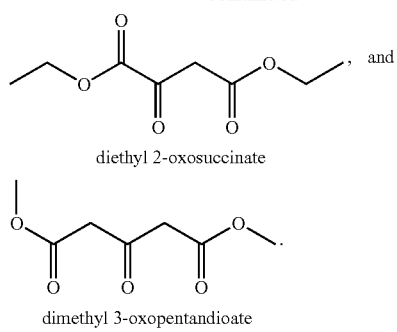

diethyl 2-oxosuccinate

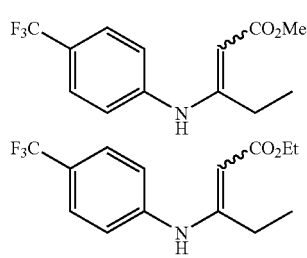

dimethyl 3-oxopentandioate

In the formula (2), a hydrocarbon group of $R^1$ is preferable, and an alkyl group is more preferable. Also, a hydrocarbon group of $R^2$ is preferable, and an alkyl group is more preferable. These $R^1$ and $R^2$ are applied to formulae below.

Specific examples of the amines of formula (3) (hereinafter called as amine (3)) include 4-trifluoromethylaniline, 3-trifluoromethylaniline, 2-trifluoromethylaniline, 3,5-bis(trifluoromethyl)aniline, 2,5-bis(trifluoromethyl)aniline, 3,4,5-tris(trifluoromethyl)aniline, 4-fluoroaniline, 3-fluoroaniline, 2-fluoroaniline, 3,4-difluoroaniline, 2,4-difluoroaniline, 2,3-difluoroaniline, 3,5-difluoroaniline, 2,3,4-trifluoroaniline, 2,4,5-trifluoroaniline, 4-chloroaniline, 3-chloroaniline, 2-chloroaniline, 3,4-dichloroaniline, 3,5-dichloroaniline, 2,3,4-trichloroaniline, 2,4,5-trichloroaniline, 3,4,5-trichloroaniline, 4-bromoaniline, 3-bromoaniline, 2-bromoaniline, 2,4-dibromoaniline, 2,5-dibromoaniline, 3,4,5-tribromoaniline, 4-iodoaniline, 3-iodoaniline, 2-iodoaniline, 4-methoxyaniline, 3-methoxyaniline, 2-methoxyaniline, etc.

In the formula (3), $R^3$ is preferably a hydrogen atom; and at least one of $R^4$ to $R^7$ is preferably a hydrogen atom, an alkoxy group, a halogenated hydrocarbon group or a halogen atom; among above, more preferably (a) $R^5$ is an alkoxy group or a halogenated hydrocarbon group, or (b) at least one of $R^4$ to $R^6$ is a halogen atom and other $R^4$ to $R^6$ and $R^7$ are each a hydrogen atom; further preferably (c) $R^5$ is an alkoxy group or a halogenated hydrocarbon group, and $R^4$, $R^6$, $R^7$ are each a hydrogen atom, or (d) $R^4$, $R^6$ are each a halogen atom and $R^5$, $R^7$ are each a hydrogen atom; furthermore preferably (e) $R^5$ is a methoxy or a fluorine-containing alkyl group of 1 to 3 carbon atoms, and $R^4$, $R^6$, $R^7$ are each a hydrogen atom, or (f) $R^4$, $R^6$ are each a chlorine atom and $R^5$, $R^7$ are each a hydrogen atom; the most preferably, $R^5$ is a trifluoromethyl and $R^4$, $R^6$, $R^7$ are each a hydrogen atom. These $R^3$ to $R^7$ are applied to formulae below.

Specific examples of enaminoesters of formula (4) (hereinafter called as enaminoesters (4)) include the following compounds:

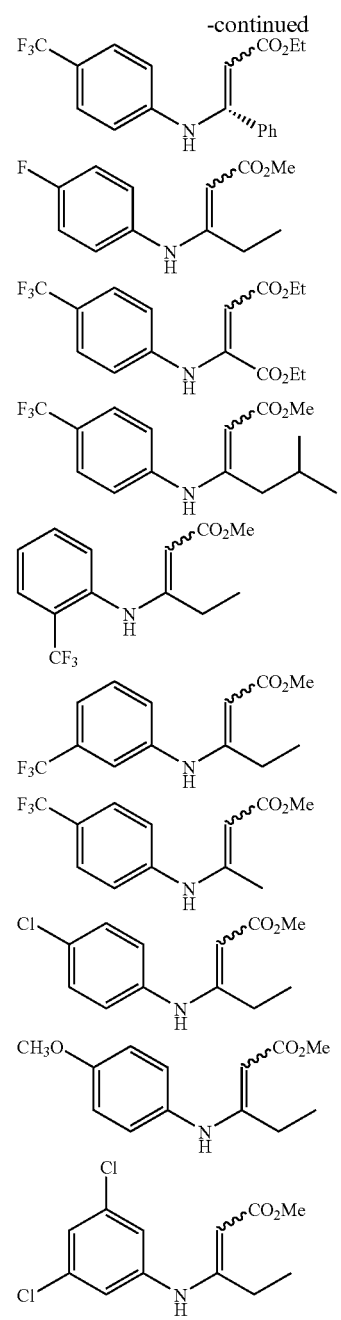

Among enaminoesters (4) obtained above, the enaminoesters of formula (9) below are used preferably:

(9)

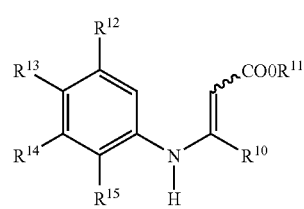

wherein $R^{10}$ is a hydrocarbon group a substituted hydrocarbon group or $COOR^{16}$ ($R^{16}$ is a hydrocarbon group or a substituted hydrocarbon group); $R^{11}$ is a hydrocarbon group or a substituted hydrocarbon group; $R^{12}$ to $R^{15}$ are each independently a hydrogen atom, a hydrocarbon group, an alkoxy group, a halogen atom or a halogenated hydrocarbon group, with the proviso that (1) when at least one of $R^{12}$ to $R^{15}$ is a halogen atom or a halogenated hydrocarbon group, and at least one of $R^{12}$ to $R^{15}$ is $CF_3$ or a bromine atom, then $R^{10}$ is a hydrocarbon group except for methyl, and that (2) when at least one of $R^{12}$ to $R^{15}$ is a halogen atom, then $R^{10}$ is a hydrocarbon group except for methyl.

The hydrocarbon group, halogen atom and halogenated hydrocarbon group are each the same as described above.

Furthermore, of the enaminoesters, enaminoesters of formula (9), wherein at least one of $R^{12}$ to $R^{15}$ is a hydrogen atom, an alkoxy group, a halogenated hydrocarbon group or a halogen atom, is preferable.

Among them, of those wherein (a) at least one of $R^{12}$ to $R^{14}$ is a halogen atom and other $R^{12}$ to $R^{14}$ and $R^{15}$ are each a hydrogen atom, or (b) $R^{13}$ is an alkoxy group or a halogenated hydrocarbon group, are preferable; and of those, wherein (c) $R^{13}$ is an alkoxy group or a halogenated hydrocarbon group, and $R^{12}$, $R^{14}$, $R^{15}$ are each a hydrogen atom, or (d) $R^{12}$, $R^{14}$ are each a halogen atom and $R^{13}$, $R^{15}$ are each a hydrogen atom, are more preferable.

Among them, of those wherein (e) $R^{13}$ is methoxy or a fluorine-containing alkyl group of 1 to 3 carbon atoms and $R^{12}$, $R^{14}$, $R^{15}$ are each a hydrogen atom, or (f) $R^{12}$, $R^{14}$ are each a chlorine atom and $R^{13}$, $R^{15}$ are each a hydrogen atom, are further preferable; and of those, wherein $R^{13}$ is trifluoromethyl and $R^{12}$, $R^{14}$, $R^{15}$ are each a hydrogen atom is most preferable.

Further, $R^{10}$ of hydrocarbon group is preferable with the proviso that (1) when at least one of $R^{12}$ to $R^{15}$ is a halogen atom or a halogenated hydrocarbon group, and at least one of $R^{12}$ to $R^{15}$ is $CF_3$ or a bromine atom, then $R^{10}$ is a hydrocarbon group except for methyl, and that (2) when at least one of $R^{12}$ to $R^{15}$ is a halogen atom, then $R^{10}$ is a hydrocarbon group except for methyl, an alkyl group is more preferable with the proviso that (1) when at least one of $R^{12}$ to $R^{15}$ is a halogen atom or a halogenated hydrocarbon group, and at least one of $R^{12}$ to $R^{15}$ is $CF_3$ or a bromine atom, then $R^{10}$ is a hydrocarbon group except for methyl, and that (2) when at least one of $R^{12}$ to $R^{15}$ is a halogen atom, then $R^{10}$ is a hydrocarbon group except for methyl, and ethyl is most preferable.

Furthermore, $R^{11}$ of hydrocarbon group is preferable, an alkyl group is more preferable, and methyl is most preferable.

Specific examples of the optically active β-amino acid derivatives of formula (5) (hereinafter called as β-amino acid derivatives (5)) include, for example compounds as follows:

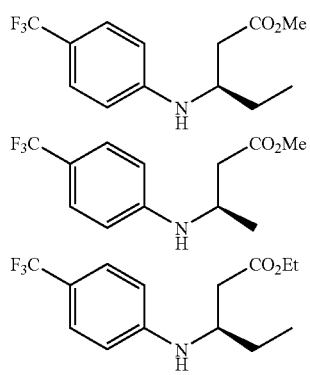

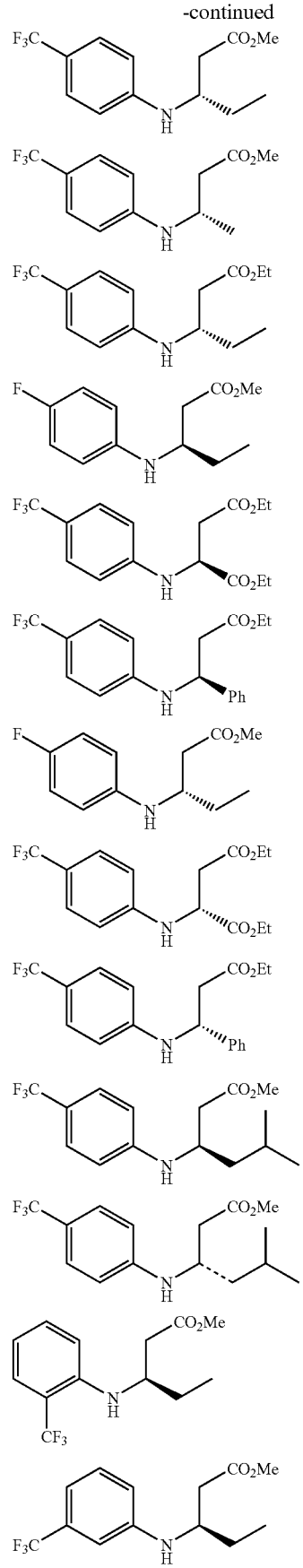

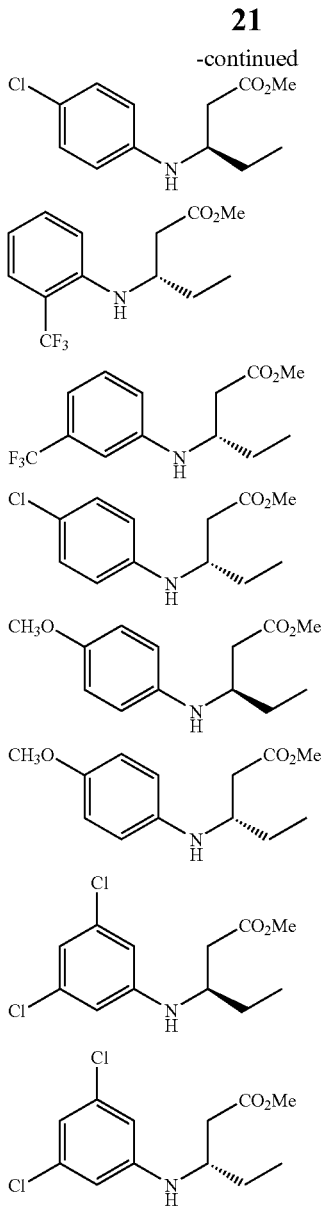

As to the optically active β-amino acid derivatives (5) obtained by the asymmetric hydrogenation, the β-amino acid derivatives of formula (15c) above are preferably obtained. Among those β-amino acid derivatives, optically active β-amino acid derivatives of formula (15),

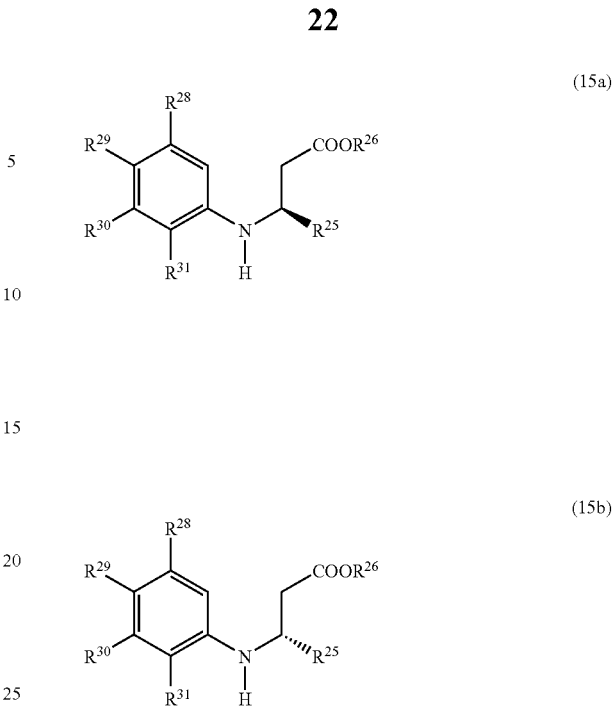

wherein * indicates an asymmetric carbon atom; $R^{25}$ to $R^{31}$ have the same meanings as mentioned above, are obtained more preferably, and optically active β-amino acid derivatives of formula (15a) and formula (15b), wherein $R^{25}$, $R^{26}$ and $R^{28}$ to $R^{31}$ have the same meanings as mentioned above, are obtained especially preferably.

Further, in formulae (15) and (15c), $R^{27}$ of a hydrogen atom is preferable.

Furthermore, of the β-amino acid derivatives of formulae (15), (15a), (15b) and (15c), wherein at least one of $R^{28}$ to $R^{31}$ is a hydrogen atom, an alkoxy group, a halogenated hydrocarbon group or a halogen atom, is preferable with the proviso that either i) $R^{27}$ or $R^{31}$ is a hydrogen atom, ii) at least one of $R^{27}$ to $R^{31}$ is a hydrocarbon group, a halogen atom, a halogenated hydrocarbon group or an alkoxy group, iii) when at least one of $R^{27}$ to $R^{31}$ is an alkoxy group, $R^{25}$ is a methyl group or an ethyl group, and iv) when at least one of $R^{27}$ to $R^{31}$ is a halogen atom or a methyl group, $R^{25}$ is a hydrocarbon group.

Among them, of those wherein (a) at least one of $R^{28}$ to $R^{30}$ is a halogen atom and other $R^{28}$ to $R^{30}$ and $R^{31}$ are each a hydrogen atom, or (b) $R^{29}$ is an alkoxy group or a halogenated hydrocarbon group, are preferable; and of those, wherein (c) —$R^{29}$ is an alkoxy group or a halogenated hydrocarbon group and $R^{28}$, $R^{30}$, $R^{31}$ are each a hydrogen atom, or (d) $R^{28}$, $R^{30}$ are each a halogen atom and $R^{29}$, $R^{31}$ are each a hydrogen atom, are more preferable.

Among them, of those wherein (e) $R^{29}$ is methoxy or a fluorine-containing alkyl group of 1 to 3 carbon atoms and $R^{28}$, $R^{30}$, $R^{31}$ are each a hydrogen atom, or (f) $R^{28}$, $R^{30}$ are each a chlorine atom and $R^{29}$, $R^{31}$ are each a hydrogen atom, are further preferable; and of those, wherein $R^{29}$ is trifluoromethyl and $R^{28}$, $R^{30}$, $R^{31}$ are each a hydrogen atom is the most preferable.

Further, $R^{25}$ of hydrocarbon group is preferable, an alkyl group is more preferable, and ethyl is the most preferable.

Furthermore, $R^{26}$ of hydrocarbon group is preferable, an alkyl group is more preferable, and methyl is the most preferable.

In formulae (15), (15a), (15b) and (15c), the hydrocarbon groups, halogen atoms and halogenated hydrocarbon groups have the same meanings as mentioned above.

Specific examples of the optically active amides of formula (6) above (hereinafter called optically active amides (6)) include the following compounds:

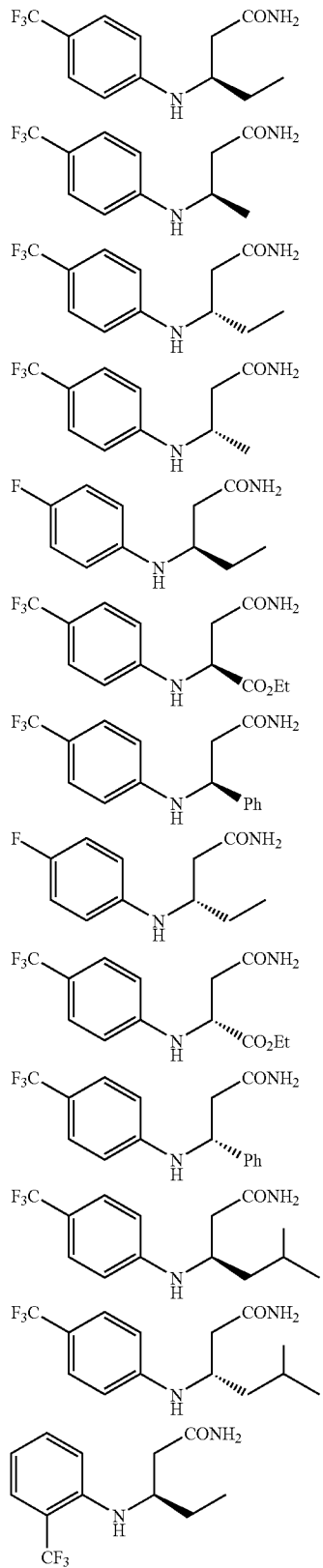

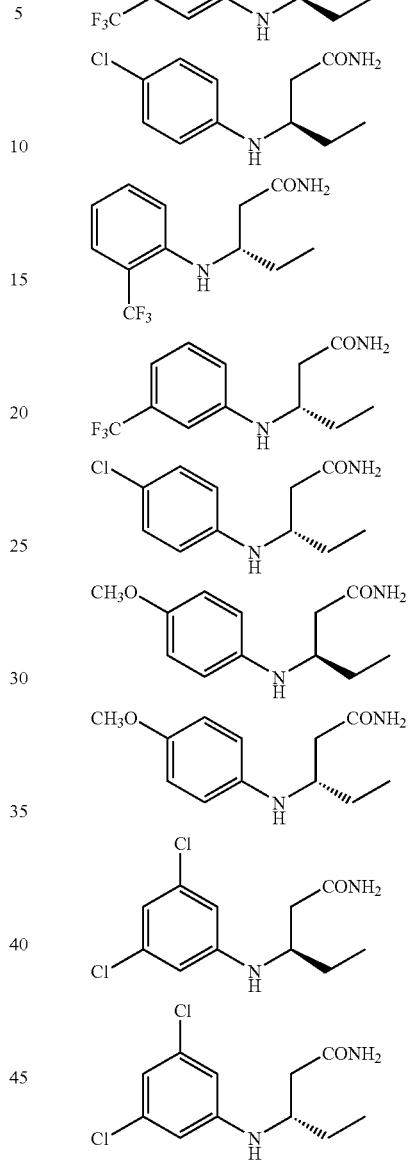

The optically active amides (6) obtained by the amidation are optically active amides (16a) below, when optically active β-amino acid derivatives (15a) above are used, and the optically active amides (6) obtained by the aimidation are optically active amides (16b) below, when the optically active β-amino acid derivatives (15b) above are used,

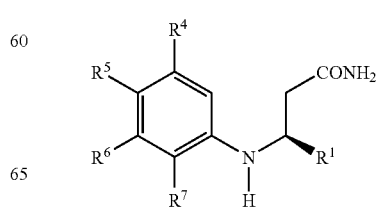

(16a)

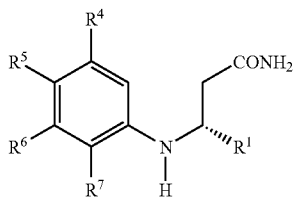

(16b)

wherein R¹ and R⁴ to R⁷ have the same meanings as mentioned above.

The compounds (7) above obtained by the alkoxycarbonylation of the amides (6) are optically active compounds (17a) below, when amides of formula (16a) above are used, and the compounds (7) are optically active compounds (17b) below, when amides of formula (16b) above are used.

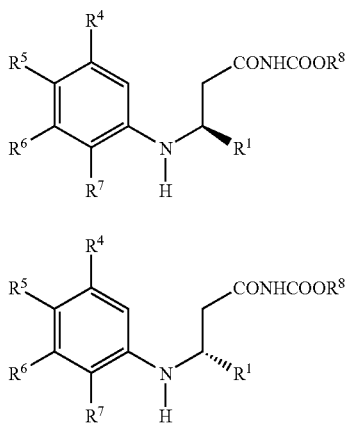

(17a)

(17b)

wherein R¹ and R⁴ to R⁸ have the same meanings as mentioned above.

Specific examples of the compounds of formula (7) above (hereinafter called compounds (7)) include the following compounds:

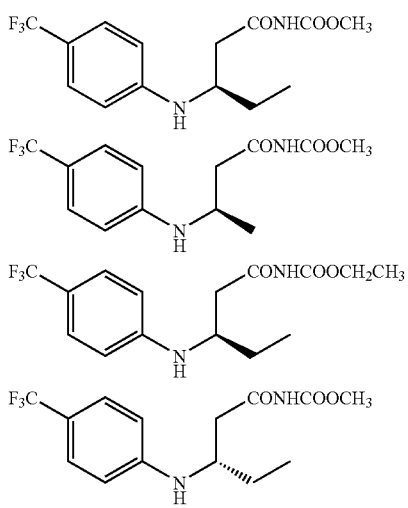

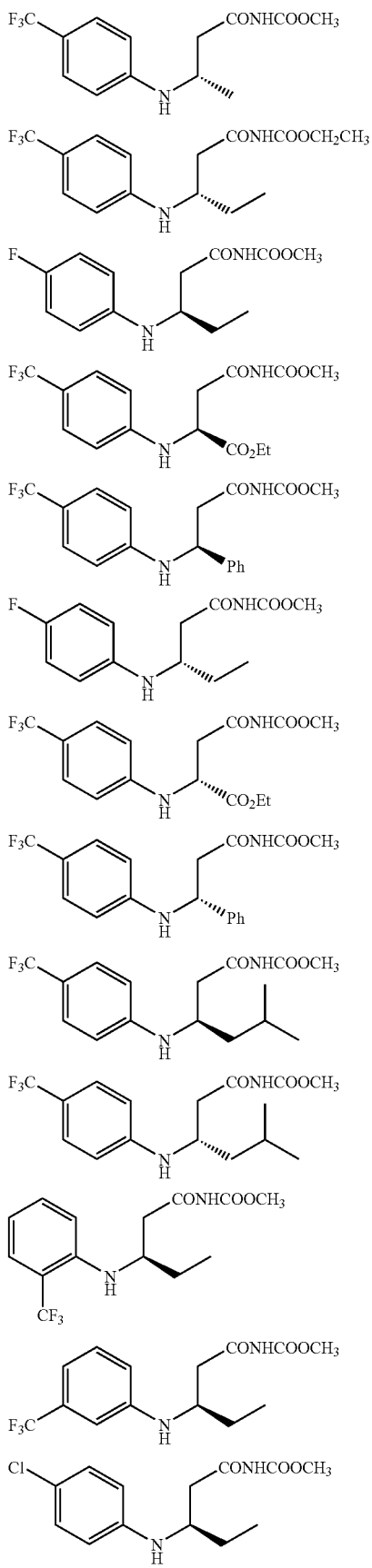

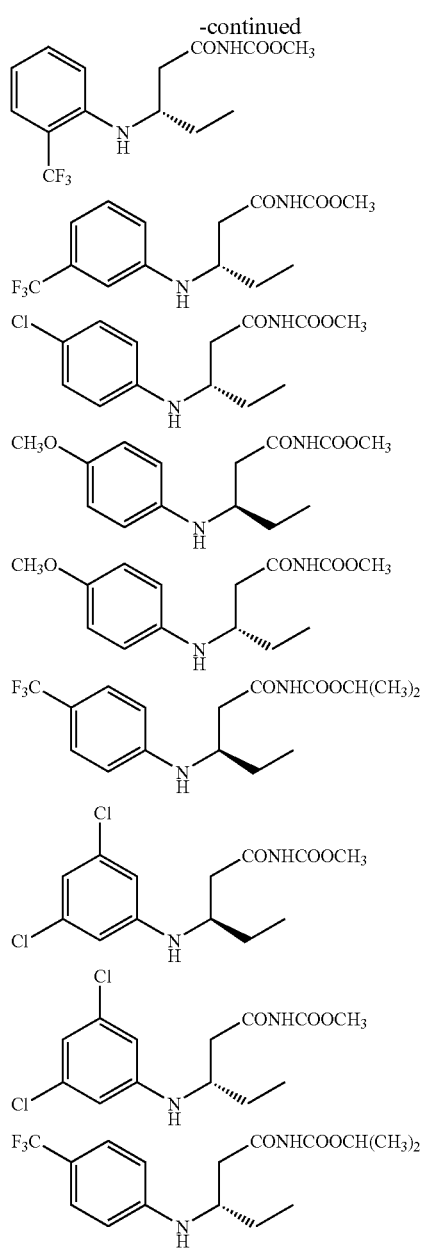
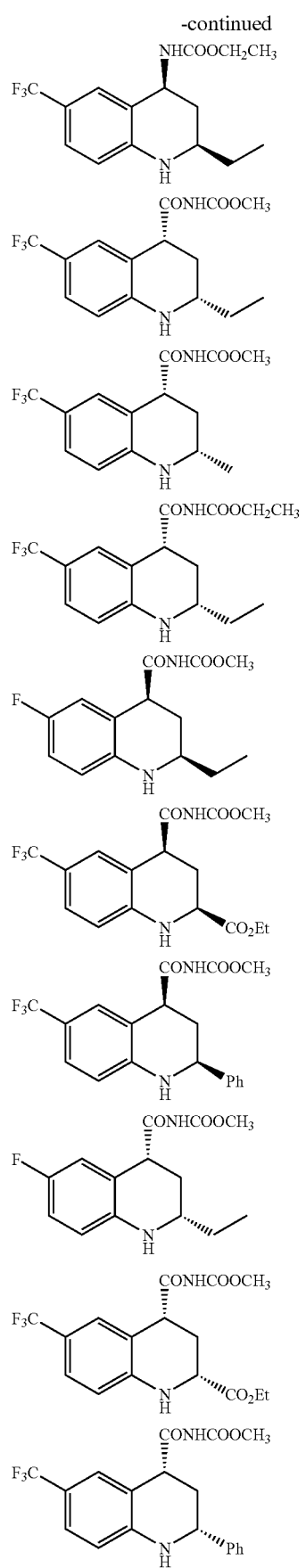
Specific examples of the optically active tetrahydroquinolines of formula (1) above (hereinafter called optically active tetrahydroquinolines (1)) include the following compounds:
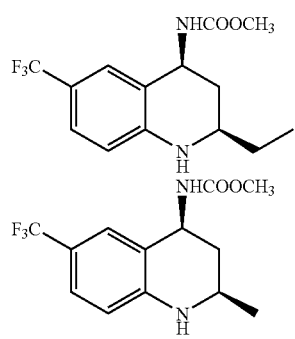

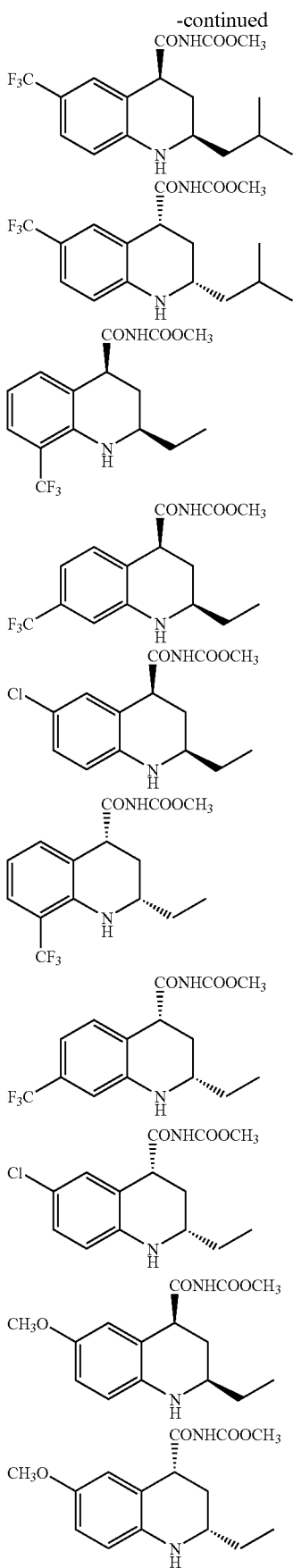

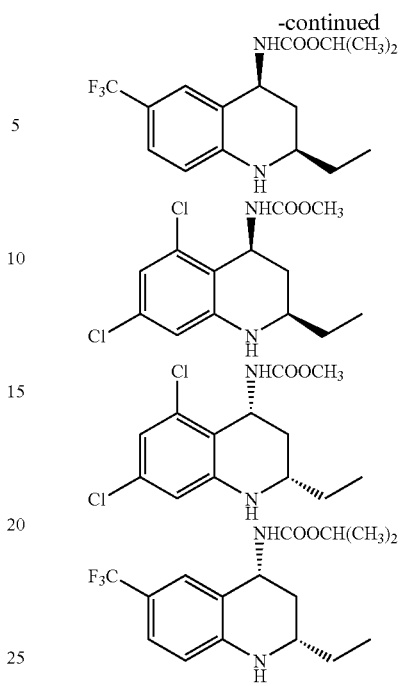

In the method for producing optically active tetrahydroquinolines (1) of the present invention, β-ketoesters (2) and amines (3) are first made to react in the presence of an acid to give enaminoesters (4).

The amount used of β-ketoesters (2) is usually selected appropriately from the range of 0.7 to 2.0 equivalents, preferably of 0.8 to 1.5 equivalents, to the amount used of amines (3).

Various acidic substances such as inorganic acids, organic acids and Lewis acids can be used as the said acid. Examples of the inorganic acids include hydrochloric acid, sulfuric acid, phosphoric acid, polyphosphoric acid. Examples of the organic acids include carboxylic acids such as formic acid, acetic acid, chloroacetic acid, dichloroacetic acid, trichloroacetic acid, trifluoroacetic acid, etc.; sulfonic acids such as benzenesulfonic acid, para-toluenesulfonic acid, methanesulfonic acid, camphorsulfonic acid, etc.; solid acids such as ion-exchange resins having functional groups such as sulfo, carboxyl, etc. Examples of the Lewis acids include titanium tetrachloride, boron trifluoride etherate, zinc chloride, scandium triflate, lanthanum triflate, tri(tert-butyl) borate. Among these acids, acetic acid, para-toluenesulfonic acid, boron trifluoride etherate, and solid acids are preferable.

The amount used of the acid can be usually selected appropriately from the range of 0.01 to 0.3 equivalent, or preferably of 0.01 to 0.2 equivalent to the amount of the amine used.

The reaction of β-ketoester (2) with amine (3) is preferably carried out in the presence of a solvent. Examples of the solvent include aliphatic hydrocarbons such as pentane, hexane, heptane, octane, decane, cyclohexane, etc; aromatic hydrocarbons such as benzene, toluene, xylene, etc.; halogenated hydrocarbons such as dichloromethane, 1,2-dichloroethane, chloroform, carbon tetrachloride, o-dichlorobenzene, etc.; ethers such as diethyl ether, diisopropyl ether, tert-butyl methyl ether, dimethoxyethane, ethyleneglycol diethyl ether, tetrahydrofuran, 1,4-dioxane, 1,3-dioxolane, etc.; alcohols such as methanol, ethanol, 2-propanol, 1-butanol, 2-ethoxyethanol, benzyl alcohol, etc.; polyalcohols such as ethylene glycol, propylene glycol, 1,2-propanediol, glycerol, etc.;

esters such as methyl acetate, ethyl acetate, n-butyl acetate, methyl propionate, etc.; amides such as formamide, N,N-dimethylformamide, N,N-dimethylacetamide, etc.; sulfoxides such as dimethyl sulfoxide, etc.; cyano-containing organic compounds such as acetonitrile, etc.; N-methylpyrolidone, and water.

These solvents may be used solely, or in optional combination of two or more solvents thereof.

The amount used of the solvent is appropriately selected usually from the range of 1 to 15 times, or more preferably from the range of 1 to 10 times the volume of amines (3).

The reaction temperature is appropriately selected usually from the range of 0 to 140° C., or more preferably from the range of 20 to 120° C.

The reaction time is appropriately selected usually from the range of 1 to 12 hours, or more preferably from the range of 1 to 10 hours.

Enaminoesters (4) obtained above are then subjected to asymmetric hydrogenation to produce optically active β-amino acid derivatives (5) above.

The asymmetric hydrogenation gives optically active β-amino acid derivatives (5) efficiently and in excellent asymmetric yields when it is carried out in the presence of asymmetric hydrogenation catalysts.

Transition metal complexes can be preferably used as the asymmetric catalysts for the asymmetric hydrogenation, and, among those transition metal complexes, those of group 8, 9, 10 metals in the periodic table of elements are preferably used.

Examples of the transition metal complexes include compounds of formula 12 and formula 13,

wherein M is a transition metal of group VIII in the periodic table of elements; L is a chiral ligand; X is a halogen atom, a carboxylato group, an allyl group, a 1,5-cyclooctadiene or a norbornadiene; Y is a ligand: Z is an anion; and m, n, p, q and s are each an integer of 0 to 5.

In formulae (12) and (13), the Ms, the group 8, 9, 10 transition metals in the periodic table of elements, are the same or different, and include ruthenium(Ru), rhodium(Rh), iridium(Ir), palladium(Pd), nickel(Ni), etc.

The chiral ligands represented by L are the same or different, and include monodentate ligands, bidentate ligands, etc. The optically active phosphine ligands are preferable, and the optically active bidentate phosphine ligands are more preferable as the chiral ligands.

Examples of the optically active bidentate phosphine ligands include phosphine compounds of formula (20),

wherein $R^a$ to $R^d$ are each independently an alkyl group, a substituted alkyl group, an aryl group, a substituted aryl group, a heterocyclic group or a substituted heterocyclic group; Q is a spacer.

The alkyl groups, substituted alkyl groups, aryl groups and substituted aryl groups represented by $R^a$ to $R^d$ can have the same meanings as those described above, and $R^a$ and $R^b$ and/or $R^c$ and $R^d$, taken together, may form a ring.

The heterocyclic groups include aliphatic heterocyclic groups and aromatic heterocyclic groups, and the substituted heterocyclic groups include substituted aliphatic heterocyclic groups and substituted aromatic heterocyclic groups. These aliphatic heterocyclic groups, aromatic heterocyclic groups, substituted aliphatic heterocyclic groups and substituted aromatic heterocyclic groups can have the same meanings as those described above.

The spacers represented by Q include divalent organic groups such as alkylene groups and arylene groups, etc. which may be substituted.

Examples of the alkylene groups include alkylene groups of 1 to 6 carbon atoms, and specific examples of them include methylene, ethylene, trimethylene, propylene, tetramethylene, pentamethylene, hexamethylene, etc. Examples of the arylene groups include arylene groups of 6 to 20 carbon atoms, and specific examples of them include phenylene, biphenyldiyl, binaphthalenediyl, etc. These divalent organic groups may be substituted with substituents such as alkyl groups, aryl groups, heterocyclic groups and alkylenedioxy groups, all of which are the same as described above.

The spacer represented by Q could be an optically active spacer. In case of ethylene group as the spacer which has no asymmetric carbon atom, at least one of the hydrogen atom in the spacer is substituted by a substituent such as phenyl group to form an optically active spacer.

Specific examples of the chiral ligands include cyclohexylanisylmethylphosphine(CAMP), 1,2-bis(anisylphenylphosphino)ethane(DIPAMP), 1,2-bis(alkylmethylphosphino)ethane(BisP*), 2,3-bis(diphenylphosphino)butane (CHIRAPHOS), 1,2-bis(diphenylphosphino)propane (PROPHOS), 2,3-bis(diphenylphosphino)-5-norbornene (NORPHOS), 2,3-O-isopropylidene-2,3-dihydroxy-1,4-bis (diphenylphosphino)butane(DIOP), 1-cyclohexyl-1,2-bis (diphenylphosphino)ethane(CYCPHOS), 1-substituted-3,4-bis(diphenylphosphino)pyrrolidine(DEGPHOS), 2,4-bis (diphenylphosphino)pentane(SKEWPHOS), 1,2-bis (substituted-phospholano)benzene(DuPHOS), 1,2-bis (substituted-phospholano)ethane(BPE), 1-((substituted-phospholano)-2-(diphenylphosphino)benzene(UCAP-Ph), 1-(bis(3,5-dimethylphenyl)phosphino)-2-(substituted-phospholano)benzene(UCAP-DM), 1-((substituted-phospholano)-2-(bis(3,5-di(t-butyl)-4-methoxyphenyl)phosphino) benzene(UCAP-DTBM), 1-((substituted-phospholano)-2-(di-naphthalen-1-ylphosphino)benzene(UCAP-(1-Nap)), bis (diphenylphosphino)ferrocenyl]ethylamine(BPPFA), 1-[1', 2-bis(diphenylphosphino)ferrocenyl]ethyl alcohol (BPPFOH), 2,2'-bis(diphenylphosphino)-1,1'-dicyclopentane(BICP), 2,2'-bis(diphenylphosphino)-1,1'-binaphthyl(BINAP), 2,2'-bis(diphenylphosphino)-1,1'-(5,5', 6,6', 7,7',8,8'-octahydrobinaphthyl)(H$_8$-BINAP), 2,2'-bis(di-p-tolylphosphino)-1,1'-binaphthyl(TOL-BINAP), 2,2'-bis(di (3,5-dimethylphenyl)phosphino)-1,1'-binaphthyl(DM-BINAP), 2,2'-bis(diphenylphosphino)-6,6'-dimethyl-1,1'-biphenyl(BICHEP), ((5,6), (5',6')-bis(methylenedioxy) biphenyl-2,2'-diyl)(bisdiphenylphosphine)(SEGPHOS), ((5, 6), (5',6')-bis(methylenedioxy)biphenyl-2,2'-diyl)(bis(3,5-dimethylphenyl)phosphine)(DM-SEGPHOS) and ((5,6), (5', 6')-bis(methylenedioxy)biphenyl-2,2'-diyl)(bis(3,5-di(tert-butyl)-4-methoxyphenyl)phosphine)(DTBM-SEGPHOS).

The word "substituted" above includes any groups as far as they do not inhibit the reaction of the present invention. Chiral ligands described above with further substituents can also be appropriately used.

The ligands represented by Y are the same or different and include neutral ligands such as aromatic compounds and olefinic compounds. Examples of the aromatic compounds include benzene, p-cymene, 1,3,5-trimethylbenzene(mesitylene) and hexamethylbenzene. Examples of the olefinc compounds include ethylene, 1,5-cyclooctadiene, cyclopentadiene and norbornadiene. Examples of the other neutral ligands include N,N-dimethylformamide (DMF), acetonitrle, benzonitrile, acetone and chloroform.

The halogen atoms represented by X include a chlorine atom, a bromine atom and an iodine atom.

The anions represented by Z in formula (13) include $BF_4$, $ClO_4$, OTf, $PF_6$, $SbF_6$, $BPh_4$, Cl, Br, I, $I_3$ and sulfonate, wherein Tf represents a triflate group ($SO_2CF_3$).

The following is the description of the preferable embodiments of the transition metal complexes mentioned above.

[1] As to formula (12):

$$M_nL_nX_pY_q \quad (12)$$

1) When M is Ir or $R^h$, X is then Cl, Br or I, and when L is a monodentate ligand, then m=p=2, n=4 and q=0; and when L is a bidentate ligand, then m=n=p=2 and q=0.
2) When M is Ru, then (i) X is Cl, Br or I, and Y is a trialkylamino group, and when L is a monodentate ligand, then m=2, n=p=4 and q=1; and when L is a bidentate ligand, then m=n=2, p=4, and q=1, or
   (ii) X is Cl, Br, or I, and Y is a pyridyl group or a pyridyl group substituted on the ring, and when L is a monodentate ligand, then m=1, n=p=2 and q=2; and when L is a bidentate ligand, then m=n=1, p=2 and q=2, or
   (iii) X is a carboxylato group, and when L is a monodentate ligand, then m=1, n=p=2 and q=0; and when L is a bidentate ligand, m=n=1, p=2 and q=0.
   (iv) X is Cl, Br or I, and when L is a monodentate ligand, then m=p=2, n=4 and q=0; and when L is a bidentate ligand, then m=n=p=2 and q=0.
3) When M is Pd, (i) X is Cl, Br or I, and when L is a monodentate ligand, then m=1, n=2, p=2 and q=0; and when L is a bidentate ligand, m=n=1, p=2 and q=0, or
   (ii) X is an allyl group, and when L is a monodentate ligand, then m=p=2, n=4 and q=0; and when L is a bidentate ligand, then m=n=p=2 and q=0.
4) When M is Ni, X is then Cl, Br or I, and when L is a monodentate ligand, then m=1, n=2, p=2 and q=0; and when L is a bidentate ligand, then m=n=1, p=2 and q=0.

[2] As to formula (13):

$$[M_mL_nX_pY_q]Z_s \quad (13)$$

1) When M is Ir or Rh, then X is 1,5-cyclooctadiene or norbornadiene, and Z is $BF_4$, $ClO_4$, OTf, $PF_6$, $SbF_6$ or $BPh_4$, and m=n=p=s=1 and q=0, or m=s=1, n=2 and p=q=0.
2) When M is Ru, then (i) X is Cl, Br or I, Y is a neutral ligand such as an aromatic compound and an olefinic compound, Z is Cl, Br, I, $I_3$ or sulfonate, and when L is a monodentate ligand, then m=p=s=q=1 and n=2; and when L is a bidentate ligand, then m=n=p=s=q=1, or
   (ii) X is Cl, Br or I, Z is $BF_4$, $ClO_4$, OTf, $PF_6$, $SbF_6$ or $BPh_4$, and when L is a monodentate ligand, then m=1, n=2, p=q=0 and s=2; and L is a bidentate ligand, then m=n=1, p=q=0 and s=2.
3) When M is Pd or Ni, then (i) Z is $BF_4$, $ClO_4$, OTf, $PF_6$, $SbF_6$ or $BPh_4$, and when L is a monodentate ligand, then m=1, n=2, p=q=0 and s=2; and when L is a bidentate ligand, then m=n=1, p=q=0 and s=2.

These transition metal complexes can be produced by using the known methods.

In addition, symbols used in the formulae of transition metal complexes below have the meanings as follows: L: a chiral ligand; cod: 1,5-cyclooctadiene; nbd: norbornadiene; Tf: a triflate group ($SO_2CF_3$); Ph: a phenyl group, and Ac: an acetyl group. Specific examples of the transition metal complexes are given below, although only those which have bidentate ligands as the chiral ligand are selected to avoid too much complexity for the explanation Rhodium complexes:

Rhodium complexes can be produced by the methods described in Jikken Kagaku Kouza, $4^{th}$ Ed., Vol. 18, Organic Metal Complexes, p. 339-344 (1991) (Edited by Nihon Kagakukai) (Maruzen), etc. or, more specifically, by reacting bis(cycloocta-1,5-diene)rhodium(I) tetrafluoroborate with a chiral ligand.

Specific examples of the rhodium complexes include those as follows:
[Rh(L)Cl]$_2$, [Rh(L)Br]$_2$, [Rh(L)I]$_2$, [Rh(cod)(L)]BF$_4$, [Rh(cod)(L)]ClO$_4$, [Rh(cod)(L)]PF$_6$, [Rh(cod)(L)]BPh$_4$, [Rh(cod)(L)]OTf, [Rh(nbd)(L)]BF$_4$, [Rh(nbd)(L)]ClO$_4$, [Rh(nbd)(L)]PF$_6$, [Rh(nbd)(L)]BPh$_4$, [Rh(nbd)(L)]OTf and [Rh(L)$_2$]ClO$_4$.

Ruthenium Complexes:

Ruthenium complexes can be produced by the methods described in the literature: T. Ikariya, Y. Ishii, H. Kawano, T. Arai, M. Saburi, S. Yoshikawa, and S. Akutagawa, J. Chem. Soc., Chem. Commun., 1985, 922, etc. More specifically, they can be produced by heating [Ru(cod)Cl$_2$]$_n$ and a chiral ligand in toluene under reflux in the presence of triethylamine.

They can also be produced by the method described in the literature: K. Mashima, K. Kusano, T. Ohta, R. Noyori, H. Takaya, J. Chem. Soc., Chem. Commun., 1989, 1208. More specifically, they can be produced by heating [Ru(p-cymene)I$_2$]$_2$ and a chiral ligand in methylene chloride and ethanol under reflux with stirring.

Specific examples of the ruthenium complexes include those as follows: Ru(OAc)$_2$(L), Ru$_2$Cl$_4$(L)$_2$NEt$_3$, [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)]I, [Ru(L)](BF$_4$)$_2$, [Ru(L)](ClO$_4$)$_2$, [Ru(L)](PF$_6$)$_2$, [Ru(L)](BPh$_4$)$_2$, [Ru(L)](OTf)$_2$, Ru(OCOCF$_3$)$_2$(L), [{Rucl(L)}$_2$(μ-cl)$_3$][Me$_2$NH$_2$] and [{RuCl(L)}$_2$(μ-Cl)$_3$][Et$_2$NH$_2$].

Iridium Complexes:

Iridium complexes can be produced by the methods described in the literature: K. Mashima, T. Akutagawa, X. Zhang, T. Taketomi, H. Kumobayashi, S. Akutagawa, J. Organomet. Chem., 1992, 428, 213), etc. More specifically, they can be produced by reacting a chiral ligand with [Ir(cod)(CH$_3$CN)$_2$]BF$_4$ in tetrahydrofuran with stirring.

Specific examples of the iridium complexes include those as follows: [Ir(L)Cl]$_2$, [Ir(L)Br]$_2$, [Ir(L)I]$_2$, [Ir(cod)(L)]BF$_4$, [Ir(cod)(L)]ClO$_4$, [Ir(cod)(L)]PF$_6$, [Ir(cod)(L)]BPh$_4$, [Ir(cod)(L)]OTf, [Ir(nbd)(L)]BF$_4$, [Ir(nbd)(L)]ClO$_4$, [Ir(nbd)(L)]PF$_6$, [Ir(nbd)(L)]BPh$_4$ and [Ir(nbd)(L)]OTf.

Palladium Complexes:

Palladium complexes can be produced by the methods described in the literature: Y. Uozumi and T. Hayashi: J. Am. Chem. Soc., 1991, 9887, etc. More specifically, they can be produced by reacting a chiral ligand with π-allyl-palladium chloride.

Specific examples of the palladium complexes include those as follows: PdCl$_2$(L), (π-allyl)Pd(L), [Pd(L)]BF$_4$, [Pd(L)]ClO$_4$, [Pd(L)]PF$_6$, [Pd(L)]BPh$_4$ and [Pd(L)]OTf.

Nickel Complexes:

Nickel complexes can be produced by the methods described in Jikken Kagaku Kouza, $4^{th}$ Ed., Vol. 18, Organic Metal Complexes, p. 376 (1991)(Edited by Nihon Kagakukai)(Maruzen), etc. They can also be obtained, according to the method described in the literature: Y.

Uozumi and T. Hayashi, J. Am. Chem. Soc., 1991, 113, 9887, by dissolving a chiral ligand and nickel chloride in a mixed solvent of 2-propanol and methanol, followed by heating with stirring.

Specific examples of the nickel complexes include those as follows: $NiCl_2(L)$, $NiBr_2(L)$ and $NiI_2(L)$.

As to the transition metal complexes mentioned above, both the ones commercially available and the ones obtained by preparation may be employed.

In addition, those complexes which prepared in situ may also be applied to the asymmetric hydrogenation.

Among the transition metal complexes used in the present invention, those having chiral ligands are used preferably, and those having chiral phosphine ligands as the said chiral ligands are used more preferably.

In the production method of the present invention, the amount used of the asymmetric hydrogenation catalyst mentioned above is appropriately selected usually from the range of 1/10 to 1/100,000 times, or preferably from the range of 1/50 to 1/10,000 times, that of enaminoesters (4) in moles, depending on the enaminoesters (4) used, the reaction vessel used, and the mode or economy of the reaction.

The asymmetric hydrogenation can be carried out, as required, in a solvent. For the said solvent, those which dissolve both the enaminoesters (4) and the asymmetric hydrogenation catalysts are preferable.

Examples of the solvent include aliphatic hydrocarbons such as pentane, hexane, heptane, octane, decane, cyclohexane, etc.; aromatic hydrocarbons such as benzene, toluene, xylene, etc.; halogenated hydrocarbons such as dichloromethane, 1,2-dichloroethane, chloroform, carbon tetrachloride, o-dichlorobenzene, etc.; ethers such as diethyl ether, diisopropyl ether, tert-butyl methyl ether, dimethoxyethane, ethyleneglycol diethyl ether, tetrahydrofuran, 1,4-dioxane, 1,3-dioxolane, etc.; alcohols such as methanol, ethanol, 2-propanol, 1-butanol, 2-butanol, tert-butanol, 2-ethoxyethanol, benzyl alcohol, etc.; polyalcohols such as ethylene glycol, propylene glycol, 1,2-propanediol, glycerol, etc.; amides such as N,N-dimethylformamide, N,N-dimethylacetamide, etc.; sulfoxides such as dimethyl sulfoxide, etc.; cyano-containing organic compounds such as acetonitrile, etc.; N-methylpyrrolidone; and water. These solvents may be used solely or in optional combination of two or more solvents thereof. Among these solvents, alcohols such as methanol, ethanol, 2-propanol, 1-butanol, 2-butanol, tert-butanol, 2-ethoxyethanol, benzyl alcohol, etc. are preferable.

The amount of the solvent used is determined considering the solubility of the enaminoesters (4) to be used and cost effectiveness. When, for example, an alcohol is used as solvent, the reaction can be carried out, with some enaminoesters (4), in concentrations ranging from less than 1% to without or almost without solvent. The amount of the solvent used is appropriately selected usually from the range of 0.1 to 10 times, or more preferably from 0.5 to 5 times, the volume of the enaminoesters (4) used.

Although atmospheric hydrogen or 1 atmosphere (atmospheric pressure) (0.1 MPa) of hydrogen is enough for the asymmetric hydrogenation, the pressure of hydrogen is appropriately selected usually from the range of 1 to 200 atm. (0.1 to 20 MPa), or more preferably of 2 to 100 atm. (0.2 to 10 MPa), considering cost effectiveness, etc. It is also possible to maintain a high activity under pressure of not higher than 10 atm. (1 MPa), considering cost effectiveness.

The reaction temperature is appropriately selected usually from the range of 15 to 120° C., or more preferably from the range of 20 to 100° C., considering cost effectiveness, etc.

However, the reaction itself can be carried out at temperatures as low as from −30 to 0° C., or at temperatures as high as 100 to 250° C.

Although the reaction time varies with the reaction conditions, etc. such as the kind and amount used of the asymmetric hydrogenation catalysts, kind and concentration used of the enaminoesters (4), reaction temperature and pressure of hydrogen, etc., the reaction is completed in a time from several minutes to several hours. The reaction time is selected usually from the range of 1 minute to 48 hours, or more preferably from the range of 10 minutes to 24 hours.

The asymmetric hydrogenation can be carried out both in a batch process and in a continuous process.

The optical purity of the optically active β-amino acid derivatives (5) obtained by the production method of the present invention is equal to or higher than 85% e.e., preferably 90% e.e.

In the amidation, the optically active amides (6) are obtained by reacting the optically active β-amino acid derivatives (5) obtained with ammonia or ammonium salts.

Examples of such ammonium salts include ammonium salt such as ammonium acetate, ammonium formate, ammonium phosphate, ammonium chloride, ammonium sulfate, etc.

The amount of the ammonia or the ammonium salts used is appropriately selected usually from the range of 0.9 to 20 moles, or more preferably from the range of 1 to 15 moles per 1 mole of the optically active β-amino acid derivatives (5).

The reaction may be carried out, if necessary, in an atmosphere of inert gases. Examples of the inert gases include nitrogen and argon.

The amidation is preferably carried out in alcoholic solvents and water. Examples of such alcoholic solvents include alcohols such as methanol, ethanol, 2-propanol, 1-butanol, 2-butanol, 2-ethoxyethanol, benzyl alcohol, etc.

These solvents may be used solely, or in optional combination of two or more solvents thereof.

The amount of the solvent used is appropriately selected usually from the range of 0.5 to 10 times, or preferably from the range of 0.5 to 5 times the volume of the optically active β-amino acid derivatives (5).

The reaction temperature is appropriately selected usually from the range of 0 to 150° C., or preferably from the range of 15 to 120° C.

The reaction time is appropriately selected usually from the range of 10 minutes to 96 hours, or more preferably from the range of 30 minute to 48 hours.

The optically active amides (6) obtained can be appropriately alkoxycarbonylated by the reaction with halogenoformates of, for example, formula (14) (hereinafter called halogenoformates),

$R^8OCOX^2$ (14)

wherein $X^2$ is a halogen atom and $R^8$ has the same meanings as mentioned above.

Examples of the halogen atoms represented by $X^2$ include a fluorine atom, a chlorine atom, a bromine atom and an iodine atom. Among them, a chlorine atom is preferable.

Examples of the halogenoformates include compounds such as methyl chloroformate, ethyl chloroformate, propyl chloroformate, butyl chloroformate, benzyl chloroformate, etc.

The amount of the halogenoformates used is appropriately selected usually from the range of 1.0 to 2.0 equivalents, or more preferably from the range of 1.0 to 1.5 equivalents to the optically active amides (6) used.

The reaction may be carried out, if necessary, in an atmosphere of inert gas. Examples of the inert gas include nitrogen and argon.

Examples of the solvent include aliphatic hydrocarbons such as pentane, hexane, heptane, octane, decane, cyclohexane, etc.; aromatic hydrocarbons such as benzene, toluene, xylene, etc.; halogenated hydrocarbons such as dichloromethane, 1,2-dichloroethane, chloroform, carbon tetrachloride, o-dichlorobenzene, etc.; ethers such as diethyl ether, diisopropyl ether, tert-butyl methyl ether, dimethoxyethane, ethyleneglycol diethyl ether, tetrahydrofuran, 1,4-dioxane, 1,3-dioxolane, etc.; ketones such as acetone, methyl ethyl ketone, methyl isobutyl ketone, cyclohexanone, etc.; esters such as methyl acetate, ethyl acetate, n-butyl acetate, methyl propionate, etc.; amides such as N,N-dimethylformamide, N,N-dimethylacetamide, etc; sulfoxides such as dimethyl sulfoxide, etc.; cyano-containing organic compounds such as acetonitrile, etc; and N-methylpyrrolidone. These solvents may be used solely or in optional combination of two or more solvents thereof.

The amount of solvent used is appropriately selected usually from the range of 1.0 to 10 times, or preferably from the range of 2.0 to 6.0 times the volume of the optically active amides (6).

The alkoxycarbonylation is preferably carried out in the presence of bases. The bases may be inorganic bases or organic bases, and examples of the inorganic bases include metal hydroxides such as sodium hydroxide, potassium hydroxide, lithium hydroxide, etc.; metal carbonates such as sodium carbonate, potassium carbonate, etc.; metal bicarbonates such as sodium bicarbonate, potassium bicarbonate, etc. and metal hydrides such as sodium hydride, etc. Examples of the organic bases include alkali metal alkoxides such as potassium methoxide, sodium methoxide, lithium methoxide, sodium ethoxide, lithium tert-butoxide, potassium tert-butoxide, etc.; and organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine, N-methylmorpholine, etc.

The amount of the base used is appropriately selected usually from the range of 1.0 to 4.0 equivalents, or more preferably from the range of 1.0 to 3.0 equivalents to the optically active amides (6).

The reaction temperature is appropriately selected usually from the range of −20 to 50° C., or more preferably from the range of −5 to 35° C.

The reaction time is appropriately selected usually from the range of 5 minutes to 8 hours, or more preferably from the range of 10 minutes to 2 hours.

The optically active compounds (7) are subjected to reduction with a reducing agent and then directly to cyclization under acidic conditions to give optically active tetrahydroquinolines (1).

Examples of the reducing agents include such reducing agents as lithium aluminum hydride, sodium borohydride, borane, etc.; and combinations of sodium borohydride with Lewis acids. Combinations of sodium borohydride with Lewis acids are preferable. Examples of the preferable Lewis acids include magnesium compounds and calcium compounds. The reduced compounds are made to cyclize under acidic conditions giving tetrahydroquinolines.

As to the amount used of the reducing agent, when a combination of sodium borohydride and a Lewis acid is used as the reducing agent, the sodium borohydride is used usually in 0.5 to 2.0 times, or more preferably in 0.5 to 1.5 times the moles of the optically active compounds (7) in mole, and the Lewis acid is used usually in 0.5 to 3.0 times, or more preferably in 0.5 to 1.5 times the moles of the compounds (7).

The reaction may be carried out, if necessary, in an atmosphere of inert gas. Examples of the inert gas include nitrogen and argon.

The cyclization is preferably carried out in a solvent. Examples of the solvent include aliphatic hydrocarbons such as pentane, hexane, heptane, octane, decane, cyclohexane, etc.; aromatic hydrocarbons such as benzene, toluene, xylene, etc.; halogenated hydrocarbons such as dichloromethane, 1,2-dichloroethane, chloroform, carbon tetrachloride, o-dichlorobenzene, etc.; ethers such as diethyl ether, diisopropyl ether, tert-butyl methyl ether, dimethoxyethane, ethyleneglycol diethyl ether, tetrahydrofuran, 1,4-dioxane, 1,3-dioxolane, etc.; alcohols such as methanol, ethanol, 2-propanol, 1-butanol, 2-butanol, 2-ethoxyethanol, benzyl alcohol, etc.; polyalcohols such as ethylene glycol, propylene glycol, 1,2-propanediol, glycerol, etc; cyano-containing organic compounds such as acetonitrile, etc; N-methylpyrrolidone; and water. These solvents may be used solely or in optional combination of two or more solvents thereof.

The amount of solvent used is appropriately selected usually from the range of 1.0 to 10.0 times, or more preferably from the range of 2.0 to 8.0 times the volume of the optically active compound (7).

The cyclization reaction is preferably carried out under acidic conditions with addition of the acids to the reaction system. Various acids, namely inorganic acids, organic acids, Lewis acids, etc., can be used as the acids. Examples of the inorganic acids include hydrochloric acid, sulfuric acid, phosphoric acid and polyphosphoric acid. Examples of the organic acids include carboxylic acids such as formic acid, acetic acid, chloroacetic acid, dichloroacetic acid, trichloroacetic acid, trifluoroacetic acid, malic acid, citric acid etc.; sulfonic acids such as benzenesulfonic acid, para-toluenesulfonic acid, methanesulfonic acid, camphor-sulfonic acid, etc.; solid acids such as ion-exchange resins containing functional groups such as sulfo, carboxyl, etc. Examples of the Lewis acids include titanium tetrachloride, boron trifluoride etherate, zinc chloride, scandium triflate, lanthane triflate, tri(tert-butyl) borate, etc. Among these acids, inorganic acids such as hydrochloric acid, sulfuric acid, phosphoric acid, etc. are preferable.

The amount used of the acid is appropriately selected usually from the range of 0.01 to 50 equivalents, or preferably from the range of 0.5 to 30 equivalents to the amount of the optically active compounds (7) used.

The reaction temperature is appropriately selected usually from the range of −30 to 80° C., or preferably from the range of −15 to 40° C.

The reaction may be carried out, if necessary, in an atmosphere of inert gas. Examples of the inert gas include nitrogen and argon.

The optically active tetrahydroquinolines (1) thus obtained are of formulae (18a) to (18d), Furthermore, the cyclization product, optically active tetrahydroquinolines (1), are those of formula (18a) and/or (18d) below, when optically active compounds of formula (17a) above are used as the optically active compounds (7), and those of formula (18b) and/or (18c) below, when optically active compounds of formula (17b) above are used:

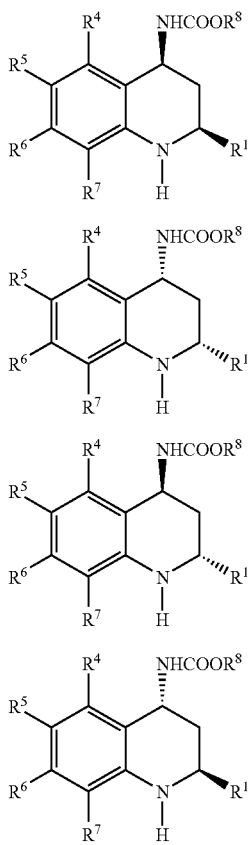

wherein, $R^1$ and $R^4$ to $R^8$ have the same meanings as mentioned above.

Among the thus obtained optically active tetrahydroquinolines of formulae (18a) to (18d) above, the tetrahydroquinolines of formulae (18a) and (18b) above are preferable, the tetrahydroquinolines of formulae (18a) above is more preferable.

The optically active tetrahydroquinolines (1) thus obtained are optically active 1,2,3,4-tetrahydroquinolines.

The production method of the present invention also makes it possible to produce optically active compounds (7) with still higher efficiency by reacting optically active β-amino acid derivatives (5) with carbamates of formula (8) (hereinafter called carbamates (8)).

Examples of the carbamates (8) include methyl carbamate, ethyl carbamate, isopropyl carbamate, butyl carbamate, and benzyl carbamate, etc.

As to the amounts used of the optically active β-amino acid derivatives (5) and the carbamates (8), the amount used of the carbamates (8) is appropriately selected usually from the range of 1.0 to 5.0 equivalents, or preferably from the range of 1.0 to 3.0 equivalents to that of optically active β-amino acid derivatives.

The reaction of the optically active β-amino acid derivatives (5) with the carbamates (8) is preferably carried out in a solvent. Examples of the solvent include aliphatic hydrocarbons such as pentane, hexane, heptane, octane, decane, cyclohexane, etc.; aromatic hydrocarbons such as benzene, toluene, xylene, etc.; halogenated hydrocarbons such as dichloromethane, 1,2-dichloroethane, chloroform, carbon tetrachloride, o-dichlorobenzene, etc.; ethers such as diethyl ether, diisopropyl ether, tert-butyl methyl ether, dimethoxyethane, ethyleneglycol diethyl ether, tetrahydrofuran, 1,4-dioxane, 1,3-dioxolane, etc.; ketones such as acetone, methyl ethyl ketone, methyl isobutyl ketone, cyclohexanone, etc.; alcohols such as methanol, ethanol, 2-propanol, 1-butanol, 2-butanol, 2-ethoxyethanol, benzyl alcohol, etc.: polyalcohols such as ethylene glycol, propylene glycol, 1,2-propanediol, glycerol, etc.; amides such as formamide, N,N-dimethylformamide, N,N-dimethylacetamide, etc; sulfoxides such as dimethyl sulfoxide, etc.; cyano-containing organic compounds such as acetonitrile, etc; and N-methylpyrrolidone. These solvents may be used solely or in optional combination of two or more solvents thereof.

The amount of solvent used is appropriately selected usually from the range of 1.0 to 10.0 times, or more preferably from the range of 2.0 to 8.0 times the volume of the optically active β-amino acid derivatives (5).

The carbamate forming reaction of the optically active β-amino acid derivatives (5) with the carbamates (8) is preferably carried out in the presence of bases. The bases may be inorganic bases, organic bases, etc. and examples of the inorganic bases include metal hydroxides such as sodium hydroxide, potassium hydroxide, lithium hydroxide, etc.; metal carbonates such as sodium carbonate, potassium carbonate, etc.; metal bicarbonates such as sodium bicarbonate, potassium bicarbonate, etc.; and metal hydrides such as sodium hydride, etc. Examples of the organic bases include alkali metal alkoxides such as potassium methoxide, sodium methoxide, lithium methoxide, sodium ethoxide, lithium tert-butoxide, potassium tert-butoxide, etc.; organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine, N-methylmorpholine, etc.

The amount used of the base is appropriately selected usually from the range of 0.5 to 3.0 equivalents, or preferably 0.8 to 2.0 equivalents to the optically active β-amino acid derivatives (5).

The reaction temperature is appropriately selected usually from the range of −20 to 80° C., or preferably of −5 to 40° C.

The reaction time is appropriately selected usually from the range of 5 minutes to 10 hours, or preferably from the range of 10 minutes to 8 hours.

The reaction may be carried out, if necessary, in an atmosphere of inert gas. Examples of the inert gas include nitrogen and argon.

In the reaction of the optically active β-amino acid derivatives (5) and the carbamates (8), the optically active compounds (7) produced are the optically active compounds of formula (17a) above, when the optically active β-amino acid derivatives of formula (15a) above are used as the optically active β-amino acid derivatives (5), and the optically active compounds of formula (17b) above, when the optically active β-amino acid derivatives of formula (15b) above are used.

In the production method of the present invention of optically active β-amino acid derivatives of formula (5a) above, said optically active β-amino acid derivatives of formula (5a) are obtained readily by subjecting the enaminoesters of formula (4a) above to asymmetric hydrogenation. Here, when R in formulae (4a) and (5a) is $OR^2$, the enaminoesters represented by formula (4a) above are enaminoesters of formula (4) above, and the optically active β-amino acid derivatives represented by formula (5a) above obtained are the optically active β-amino acid derivatives of formula (5) above.

The optical purity of the optically active tetrahydro-quinolines (1) obtained by the production method of the present invention equal to or higher than 85% e.e., preferably 90% e.e.

In the production method of the present invention of optically active β-amino acid derivatives of formula (22) above, said optically active β-amino acid derivatives of formula (22) can be obtained readily by subjecting the enamino compounds of formula (21) above to asymmetric hydrogenation.

In formulae (21) and (22), the terms: a hydrocarbon group, an aliphatic heterocyclic group, an aromatic heterocyclic group, an aryloxy group, an alkoxycarbonyl group, an aryloxycarbonyl group, an acyloxy group, a substituted hydrocarbon group, a substituted aryl group, a substituted aralkyl group, a substituted aliphatic heterocyclic group, a substituted aromatic heterocyclic group, a substituted alkoxy group, a substituted aryloxy group, a substituted aralkyloxy group, a substituted amino group, etc. have the same meanings as mentioned above.

Furthermore, in formula (22),

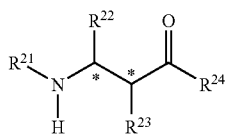

(22)

wherein symbols have each the same meaning as mentioned above, when $R^{22}$ is a hydrogen, the carbon atom to which $R^{22}$ binds is not an asymmetric carbon atom, and when $R^{23}$ is a hydrogen atom, the carbon atom to which $R^{23}$ binds is not an asymmetric carbon atom.

The asymmetric hydrogenation of the present invention of enamino compounds of formula (21)

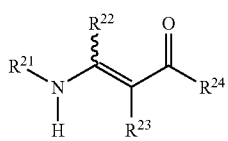

(21)

gives the optically active β-amino acid derivatives represented by formula (22) above efficiently and in excellent asymmetric yields.

Specific examples of the enamino compounds of formula (21) include, in addition to the compounds specifically exemplified above as enaminoesters (4), compounds as follows.

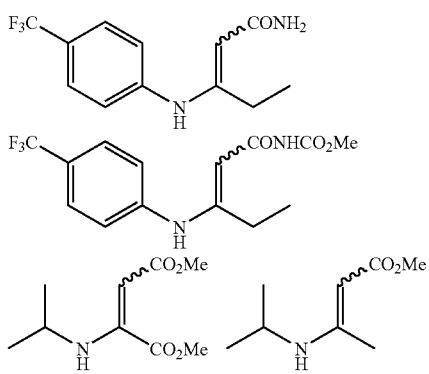

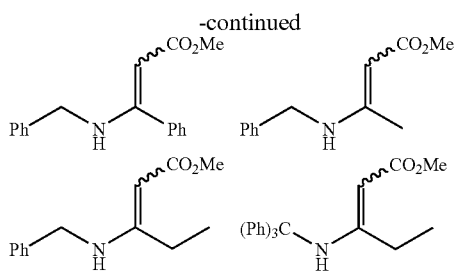

Specific examples of the optically active β-amino acid derivatives of formula (22) include, in addition to the compounds specifically exemplified above as optically active β-amino acid derivatives (5), compounds as follows.

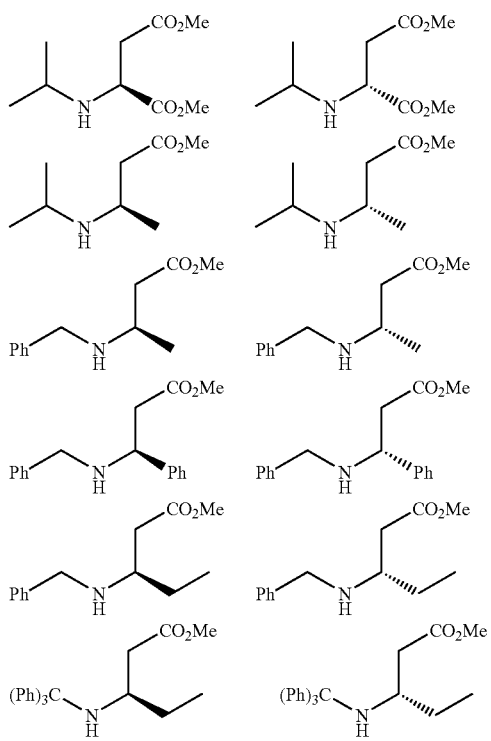

The asymmetric hydrogenation catalysts, solvents, reaction conditions, and so on which are used in the asymmetric hydrogenation, are the same as those described above in the asymmetric hydrogenation of the enaminoesters (4).

EXAMPLES

The present invention will be described in more detail referring to Examples, although the present invention is not restricted to these Examples.

The apparatus used for measuring physical characteristics, etc. in Examples below is as follows:

(1) Nuclear Magnetic Resonance Spectrum:

DRX 500 (BRUKER JAPAN Co. Ltd.), $^1$H-NMR (500.13 MHz), $^{13}$C-NMR (125.76 MHz)

(2) Gas chromatography (GLC): Hewlett Packard 5890-II (3) High Performance Liquid Chromatography (HPLC): Shimadzu LC10AT & SPD 10A

Example 1

Preparation of methyl 3-(4-trifluoromethylphenylamino)-2-pentenoate

In a 500-ml flask, 4-trifluoromethylaniline (80.6 g, 0.5 mol), methyl 3-oxopentanoate (65.1 g, 0.5 mol) and toluene 400 ml were placed. To this solution was added boron trifluoride etherate (1.42 g, 10 mmol), and the resulting mixture was heated under a reduced pressure of 8 kPa. The reaction mixture was heated for 5 hours under reflux, while water produced was removed out of the reaction system by using a Dean-Stark trap. Then, the heating was discontinued and nitrogen was leaked. After cooling, the solvent was removed by distillation by using a rotary evaporator. The residue was then distilled under reduced pressure to give 105.3 g of the title compound. The yield was 77.1%.

$^1$H-NMR (CDCl$_3$, δppm): 10.52 (bs, 1H), 7.57 (d, J=8.5 Hz, 2H), 7.16 (d, J=8.5 Hz, 2H), 4.85 (s, 1H), 3.70 (s, 3H), 2.42 (d, J=7.4 Hz, 2H), 1.08 (t, J=7.4 Hz, 3H).

Example 2

Preparation of methyl 3(R)-3-(4-trifluoromethylphenylamino) pentanoate

Methyl 3-(4-trifluoromethylphenylamino)-2-pentenoate (100 g. 0.366 mol), 2-propanol (200 ml) and [{RuCl((R)-segphos)}$_2$(μ-Cl)$_3$][Me$_2$NH$_2$] (301 mg, 0.183 mmol) were placed in a 1L-autoclave under atmosphere of nitrogen, and hydrogenation was carried out at 95° C., under a hydrogen pressure of 5 MPa for 2 hours (conversion: 100%). The solvent was removed by evaporation under reduced pressure, and the residue was distilled under reduced pressure (bp 120° C./400 Pa) to give 85.6 g of the title compound (a liquid). The yield was 85.0%.

Chemical purity: 100%
Optical purity: 96.0% e.e.
$^1$H-NMR (CDCl$_3$, δppm): 7.39 (d, J=8.3 Hz, 2H), 6.62 (d, J=8.5 Hz, 2H), 4.13 (bs, 1H), 3.81-3.77 (m, 1H), 3.66 (s, 3H), 2.55 (d, J=6.1 Hz, 2H), 1.68-1.58 (m, 2H), 0.97 (t, J=7.4 Hz, 3H).

Example 3

Preparation of methyl 3(S)-3-(4-trifluoromethylphenylamino)-2-pentanoate

Methyl 3-(4-trifluoromethylphenylamino)-2-pentenoate (190 g, 0.695 mol), 2-propanol (380 ml), [{RuCl((S)-segphos)}$_2$(μ-Cl)$_3$][Me$_2$NH$_2$] (572.5 mg, 0.348 mmol) were placed in a 1L-autoclave in a stream of nitrogen, and hydrogenation was carried out at 95° C. under a hydrogen pressure of 5 MPa for 1.5 hours (conversion: 100%). The solvent was removed by evaporation under reduced pressure, and the residue was distilled under reduced pressure (bp 120° C./400 Pa) to give 160.0 g of the title compound (a liquid). The yield was 84.0%.

Chemical purity: 100%
Optical purity: 93.1% e.e.
$^1$H-NMR (CDCl$_3$, δppm): 7.39 (d, J=8.3 Hz, 2H), 6.62 (d, J=8.5 Hz, 2H), 4.13 (bs, 1H), 3.81-3.77 (m, 1H), 3.66 (s, 3H), 2.55 (d, J=6.1 Hz, 2H), 1.68-1.58 (m, 2H), 0.97 (t, J=7.4 Hz, 3H).

Example 4

Preparation of 3(R)-3-(4-trifluoromethylphenylamino)pentanamide

Methyl 3(R)-3-(4-trifluoromethylphenylamino)pentanoate (5.5 g, 20.0 mmol) and 12.8% ammonia-methanol solution (26.6 g, 200 mmol) were placed in a 100-ml autoclave. The mixture was made to react at 100° C. for 48 hours. After cooling to room temperature, the solvent was removed by evaporation and the residue purified by chromatography on silica gel to give 3.0 g of the title compound as crystals. The yield was 57.7%.

Optical purity: 96% e.e.
$^1$H-NMR (CDCl$_3$, δppm): 7.39 (d, J=8.7 Hz, 2H), 6.65 (d, J=8.6 Hz, 2H), 5.59 (bs, 1H), 5.46 (bs, 1H), 4.29 (bd, J=6.4 Hz, 1H), 3.81-3.74 (m, 1H), 2.47 (dd, J=5.5 Hz, 15.1 Hz, 1H), 2.43 (dd, J=5.8 Hz, 15.0 Hz, 1H), 1.75-1.62 (m, 2H), 0.99 (t, J=7.4 Hz, 3H).

Example 5

Preparation of methyl 3(R)-3-(4-trifluoromethylphenylamino)pentanoylcarbamate In an atmosphere of nitrogen, 3(R)-3-(4-trifluoromethylphenylamino)-2-pentanamide (3.0 g, 11.5 mmol) and methyl chlorocarbonate (1.35 g, 14.3 mmol) were mixed in 15 ml of diisopropyl ether, and the mixture was stirred under cooling with ice. To this solution, a THF-hexane solution of lithium tert-butoxide prepared from 1.6-M n-butyllithium (15.2 ml, 24.3 mmol) and tert-butanol (1.8 g, 24.3 mmol) was added dropwise at the temperature of not more than 5° C. After completion of the addition, the mixture was stirred at the same temperature for 30 minutes. Then, the reaction was quenched with 1M hydrochloric acid. The organic layer was separated, washed successively with a saturated solution of sodium chloride and water. The solvent was then removed by evaporation to give 3.41 g of the title compound. The yield was 93%.

Optical purity: 96% e.e.
$^1$H-NMR (acetone-d$_6$, δppm): 9.36 (bs, 1H), 7.37 (d, J=8.6 Hz, 2H), 6.77 (d, J=8.6 Hz, 2H), 5.46 (bd, J=8.9 Hz, 1H), 4.00-3.93 (m, 1H), 3.69 (s, 3H), 2.96 (dd, J=6.2 Hz, 16.2 Hz, 1H), 2.86 (dd, J=6.3 Hz, 16.1 Hz, 1H), 1.77-1.68 (m, 1H), 1.66-1.57 (m, 1H), 0.97 (t, J=7.5 Hz, 3H).

Example 6

Preparation of methyl 3(R)-3-(4-trifluoromethylphenylamino)pentanoylcarbamate In a Schlenk-tube of which atmosphere had been replaced with nitrogen, 60% sodium hydride (60 mg, 1.5 mmol) was suspended in tetrahydrofuran (THF) (1 ml). To this suspension was added dropwise a THF (1 ml) solution of methyl carbamate (255 mg, 3.4 mmol) at room temperature. After stirring for 10 minutes, a solution of methyl 3(R)-3-(4-trifluoromethylphenylamino)pentanoate (500 mg, 1.8 mmol) in THF (1 ml) was added dropwise and the resulting solution was stirred for 1 hour. The reaction mixture was poured into a mixture of ethyl acetate and a saturated aqueous solution of sodium bicarbonate. The organic layer was separated and the water layer was further extracted twice with ethyl acetate. The organic layers were combined, dried over magnesium sulfate, filtered and concentrated under reduced pressure. The residue was purified by chromatography on silica gel to give 334 mg of the title compound as white crystals. The yield was 58%.

Optical purity: 96% e.e.

The $^1$H-NMR spectrum of the product was identical to that of Example 5.

Example 7

Preparation of methyl (2R,4S)-(2-ethyl-6-trifluoromethyl-1,2,3,4-tetrahydroquinolin-4-yl)carbamate In an atmosphere of nitrogen, methyl 3(R)-3-(4-trifluoromethylphenylamino)pentanoyl carbamate (1.0 g, 3.1 mmol) and 95% ethanol (6.3 ml) were mixed and the mixture was stirred at room temperature. To this solution was added sodium borohydride (83 mg, 2.2 mmol), and the resulting mixture was stirred at room temperature for 30 minutes and then cooled to −10° C. To the resulting suspension was added an aqueous solution of magnesium chloride (579 mg, 285 mmol) at a temperature not more than −5° C. The mixture was stirred at 0° C. for 1 hour, and then added dropwise to a mixture of a solution of citric acid monohydrate (1.45 g, 6.9 mmol) in 1M hydrochloric acid and methylene chloride (20 ml). The resulting mixture was stirred at room temperature for 2 hours. The organic layer was separated and treated with an aqueous solution of citric acid monohydrate (660 mg, 3.1 mmol) in water (6 ml) with stirring at room temperature for 1 hour. The organic layer was separated, washed with water, and the solvent was removed by evaporation to give 845 mg of the title compound. The yield was 89%.

Optical purity: 96% e.e.

$^1$H-NMR (acetone-$d_6$, δppm): 7.31 (bs, 1H), 7.19 (d, J=8.5 Hz, 1H), 6.65 (d, J=8.4 Hz, 1H), 6.51 (bd, J=9.0Hz, 1H), 5.61 (bs, 1H), 4.95-4.90 (m, 1H), 3.67 (s, 3H), 3.51-3.46 (m, 1H), 2.21-2.17 (m, 1H), 1.65-1.54 (m, 3H), 1.00 (t, J=7.5 Hz, 3H).

Example 8

Preparation of methyl 3(R)-3-(4-trifluoromethylphenylamino)pentanoate

Methyl 3-(4-trifluoromethylphenylamino)-2-pentenoate (100 g, 0.366 mol), 2-propanol (150 ml) and [{RuCl((R)-segphos)}$_2$(μ-Cl)$_3$][Me$_2$NH$_2$] (301 mg, 0.183 mmol) were placed in a 1L-autoclave in a stream of nitrogen, and hydrogenation was carried out at 95° C. under a hydrogen pressure of 5 MPa for 6 hours (conversion: 100%). The solvent was removed by evaporation under reduced pressure, and the residue was distilled under reduced pressure (bp 120° C./400 Pa) to give 91.4 g of the title compound (a liquid). The yield was 90.7%.

Chemical purity: 100%

Optical yield: 94.0% e.e.

The $^1$H-NMR spectrum was identical to that of Example 2.

Example 9

Preparation of 3(R)-3-(4-trifluoromethylphenylamino)pentanoate

Methyl 3-(4-trifluoromethylphenylamino)-2-pentenoate (100 g, 0.366 mol), 2-propanol (150 ml) and [{RuCl((R)-t-binap)}$_2$(μ-Cl)$_3$][Me$_2$NH$_2$] (326 mg, 0.183 mmol) were placed in a 1L-autoclave in a stream of nitrogen, and hydrogenation was carried out at 95° C. under a hydrogen pressure of 3 MPa for 6 hours (conversion: 100%). The solvent was removed by evaporation under reduced pressure, and the residue was distilled under reduced pressure (bp 120° C./400 Pa) to give 81.8 g of the title compound (a liquid). The yield was 81.2%.

Chemical purity: 100%

Optical purity: 94.2% e.e.

The $^1$H-NMR spectrum was identical to that of Example 2.

Example 10

Preparation of methyl 3(S)-3-(4-trifluoromethylphenylamino)pentanoate

Methyl 3-(4-trifluoromethylphenylamino)-2-pentenoate (190 g, 0.695 mol), 2-butanol (380 ml) and [Ru(p-cymene)Cl((S)-segphos)]Cl (637 mg, 0.695 mmol) were placed in a 1L-autoclave in a stream of nitrogen, and hydrogenation was carried out at 75° C., under a hydrogen pressure of 5 MPa for 14 hours (conversion; 100%). The solvent was removed by evaporation under reduced pressure, and the residue was distilled under reduced pressure (bp 120° C./400 Pa) to give 130.3 g of the title compound (a liquid). The yield was 68.1%.

Chemical purity: 100%.

Optical purity: 96.7% e.e.

The $^1$H-NMR spectrum was identical to that of Example 3.

Example 11

Preparation of methyl 3-(4-trifluoromethylphenylamino)-2-pentenoate

In a 1L-flask were placed 4-trifluoromethylaniline (161 g, 1.00 mol), methyl 3-oxopentanoate (130 g, 1.00 mol) and toluene (160 mL). To this solution was added acetic acid (16 g, 0.27 mol), and the resulting mixture was heated in a bath kept at 100° C. under a reduced pressure of 19 kPa for 3.5 hours, while the water generated was taken out of the reaction system by using a Dean-Stark trap under reflux. Acetic acid (16 g, 0.27 mol) was then added, and reflux was continued for 4.5 hours. Acetic acid (8 g, 0.13 mol) was then added again, and reflux was continued for another 2.5 hours. The heating was then discontinued, nitrogen leaked in, and the reaction mixture cooled. After distillation of the solvent and acetic acid under reduced pressure, the residue was distilled under reduced pressure to give 199 g of the title compound. The yield was 72.8%. The $^1$H-NMR spectrum was identical to that of Example 1.

Example 12

Preparation of methyl 3-(4-trifluoromethylphenylamino)-2-pentenoate

In a 2L-flask were placed 4-trifluoromethylaniline (161 g, 1.00 mol), methyl 3-oxopentanoate (143 g, 1.10 mol) and toluene (640 ml). To this solution was added p-toluenesulfonic acid monohydrate (3.2 g, 0.017 mol), and the resulting mixture was heated in a bath kept at 100° C. under a reduced pressure of 27 kPa, while the water generated was taken out of the reaction system by using a Dean-Stark trap under reflux. After 15 hours, the heating was discontinued, nitrogen leaked in, and the reaction mixture cooled. The solvent was evaporated by means of a rotary-evaporator, and the residue was distilled under reduced pressure to give 207 g of the title compound. The yield was 75.8%.

The $^1$H-NMR spectrum was identical to that of Example 1.

Example 13

Preparation of methyl 3-(4-trifluoromethylphenylamino)-2-pentenoate

In a 500 ml-flask were placed 4-trifluoromethylanline (48.3 g, 0.30 mol), methyl 3-oxopentanoate (43.0 g, 0.33 mol) and toluene (192 ml). To this solution was added 4.8 g of solid acid catalyst (Amberlyst No. 31 WET type, product of Rohm and Haas Co.), and the resulting mixture was heated in a bath kept at 100° C. under a reduced pressure of 25 kPa for 11 hours, while removing the water formed under reflux by using a Dean-Stark trap. The heating was then discontinued, nitrogen leaked in, and the reaction mixture cooled. The catalyst was filtered off and the solvent evaporated off by using a rotary evaporator, and the residue was distilled under reduced pressure to give 213 g of the title compound. The yield was 77.8%.

The $^1$H-NMR spectrum was identical to that of Example 1.

Example 14

Preparation of methyl 3-(4-trifluoromethylphenylamino)-2-pentenoate

4-Trifluoromethylanline (161 g, 1.00 mol), methyl 3-oxopentanoate (143 g, 1.10 mol) and toluene (640 ml) were placed in a 2L-flask. To this solution was added tri(tert-butyl) borate (22.7 g, 0.10 mol), and the resulting mixture was heated in a bath kept at 100° C. under a reduced pressure of 27 kPa for 6 hours, while removing the water formed by refluxing by using a Dean-Stark trap. The heating was then discontinued, nitrogen leaked in, and the reaction mixture cooled. The solvent was evaporated off by using a rotary-evaporator, and the residue was distilled under reduced pressure to give 212 g of the title compound. The yield was 77.6%.

The $^1$H-NMR spectrum was identical to that of Example 1.

Example 15

Preparation of methyl 3-(2-trifluoromethylphenylamino)-2-pentenoate

In a 100 ml-flask were placed 2-trifluoromethylanline (25.0 g, 155 mmol), methyl 3-oxopentanoate (22.2 g, 171 mmol) and toluene (100 ml). To this solution was added p-toluenesulfonic acid monohydrate (0.15 g, 0.79 mmol), and the resulting mixture was heated in a bath kept at 100° C. under a reduced pressure of 27 kPa for 5 hours, while removing the water formed by refluxing by using a Dean-Stark trap. The heating was then discontinued, nitrogen leaked in, and the reaction mixture cooled. After evaporation of the solvent by using a rotary evaporator, the residue was distilled under reduced pressure to give 14.0 g of the title compound. The yield was 32.7%.

$^1$H-NMR (CDCl$_3$, δppm): 10.28 (bs, 1H), 7.68 (d, J=7.3 Hz, 1H), 7.52 (t, J=7.5 Hz, 1H), 7.30 (t, J=7.7 Hz, 1H), 7.21 (d, J=8.0 Hz, 1H), 4.86 (s, 1H), 3.71 (s, 3H), 2.25 (q, J=7.5 Hz, 2H) and 1.00 (t, J=2.5 Hz, 3H).

Example 16

Preparation of methyl 3-(3-trifluoromethylphenylamino)-2-pentenoate

In a 100 ml-flask were placed 3-trifluoromethylanline (20.0 g, 124 mmol), methyl 3-oxopentanoate (17.8 g, 136 mmol) and toluene (80 ml). To this solution was added p-toluenesulfonic acid monohydrate (0.12 g, 0.62 mmol), and the resulting mixture was heated in a bath kept at 100° C. under a reduced pressure of 29 kPa for 2.5 hours, while removing the water formed by refluxing by using a Dean-Stark trap. The heating was then discontinued, nitrogen leaked in, and the reaction mixture cooled. The solvent was evaporated off by using a rotary evaporator, and the residue was distilled under reduced pressure to give 24.4 g of the title compound. The yield was 71.9%.

$^1$H-NMR (CDCl$_3$, δppm): 10.42 (bs, 1H), 7.46-7.39 (m, 2H), 7.34 (s, 1H), 7.27 (d, J=6.5 Hz, 1H), 4.82 (s, 1H), 3.70 (s, 3H), 2.36 (q, J=7.5 Hz, 2H), 1.07 (t, J=7.5 Hz, 3H).

Example 17

Preparation of methyl 3-(4-chlorophenylamino)-2-pentenoate

In a 300 ml-flask were placed 4-chloroaniline (25.0 g, 196 mmol), methyl 3-oxopentanoate (28.1 g, 216 mmol) and toluene (100 ml). To this solution was added p-toluenesulfonic acid monohydrate (0.19 g, 0.98 mmol), and the resulting mixture was heated in a bath kept at 100° C. under a reduced pressure of 23 kPa for 2.5 hours, while removing the water formed by refluxing by using a Dean-Stark trap. The heating was then discontinued, nitrogen leaked in, and the reaction mixture cooled. The solvent was evaporated off by using a rotary evaporator, and the residue was distilled under reduced pressure to give 33.1 g of the title compound. The yield was 70.5%.

$^1$H-NMR (CDCl$_3$, δppm): 10.25 (bs, 1H), 7.29 (d, J=6.6 Hz, 2H), 7.03 (d, J=6.7 Hz, 2H), 4.76 (s, 1H), 3.69 (s, 3H), 2.30 (q, J=7.5 Hz, 2H), 1.04 (t, J=7.5 Hz, 3H).

Example 18

Preparation of methyl 3-(4-trifluoromethylphenylamino)-2-butenoate

In a 1L-flask were placed 4-trifluoromethylanline (120 g, 0.745 mol), methyl acetoacetate (130 g, 1.12 mol) and toluene (360 ml). To this solution was added p-toluenesulfonic acid monohydrate (0.6 g, 0.003 mol), and the resulting mixture was heated in a bath kept at 100° C. under a reduced pressure of 27 kPa for 3 hours, while removing the water formed by refluxing by using a Dean-Stark trap. The heating was then discontinued, nitrogen leaked in, and the reaction mixture cooled. The solvent was evaporated off by using a rotary-evaporator, and the residue was distilled under reduced pressure to give 126 g of the title compound. The yield was 65.3%.

$^1$H-NMR (CDCl$_3$, δppm): 7.42 (d, J=7.8 Hz, 1H), 7.35 (t, J=7.8 Hz, 1H), 6.79 (d, J=8.3 Hz, 1H), 6.70 (t, J=7.6 Hz, 1H), 4.41 (bs, 1H), 3.89-3.81 (m, 1H), 3.68 (s, 3H), 2.62 (dd, J=5.6 Hz, 15.2 Hz, 1H), 2.52 (dd, J=6.6 Hz, 15.2 Hz, 1H), 1.73-1.50 (m, 2H), 0.98 (t, J=7.4 Hz, 3H).

Example 19

Preparation of methyl 3(R)-3-(2-trifluoromethylphenylamino)pentanoate

Methyl 3-(2-trifluoromethylphenylamino)-2-pentenoate (10.0 g, 36.6 mmol), 2-butanol (20 ml) and [RuCl(p-cymene) ((R)-segphos]Cl (33.6 mg, 0.037 mmol) were placed in a 200 ml-autoclave in a stream of nitrogen, and asymmetric hydrogenation was carried out at 70° C., under a hydrogen pressure of 3 MPa for 6 hours (conversion: 100%). The solvent was evaporated off under reduced pressure, and the residue was distilled under reduced pressure to give 9.1 g of the title compound (a liquid). The yield was 91%.

Chemical purity: 100%,
$^1$H-NMR (CDCl$_3$, δppm): 7.42 (d, J=7.8 Hz, 1H), 7.35 (t, J=7.8 Hz, 1H), 6.79 (d, J=8.3 Hz, 1H), 6.70 (t, J=7.6 Hz, 1H), 4.41 (bd, J=7.8 Hz, 1H), 3.89-3.81 (m, 1H), 3.68 (s, 3H), 2.57 (ddd, J=5.6 Hz, 15.2 Hz, 29.6 Hz, 2H), 1.73-1.50 (m, 2H), 0.98 (t, J=7.4 Hz, 3H).

Example 20

Preparation of methyl 3(R)-3-(3-trifluoromethylphenylamino)pentanoate

Methyl 3-(3-trifluoromethylphenylamino)-2-pentenoate (2.0 g, 7.3 mmol), 2-butanol (4.0 ml), [RuCl(p-cymene)((R)-segphos)]Cl (13.4 mg, 0.015 mmol) were placed in a 100 ml-autoclave in a stream of nitrogen, and asymmetric hydrogenation was carried out at 70° C., under a hydrogen pressure of 5 MPa for 16 hours (conversion: 100%). The solvent was removed by evaporation under reduced pressure, and the residue was distilled under reduced pressure to give 1.2 g of the title compound (a liquid). The yield was 60%.

Chemical purity: 100%
Optical purity: 91.5% e.e.
$^1$H-NMR (CDCl$_3$, δppm): 7.24 (t, J=8.4 Hz, 1H), 6.91 (d, J=7.7 Hz, 1H), 6.81 (s, 1H), 6.76 (d, J=8.2 Hz, 1H), 3.98 (bs, 1H), 3.81-3.73 (m, 1H), 3.66 (s, 3H), 2.54 (d, J=5.9 Hz, 2H), 1.70-1.57 (m, 2H), 0.98 (t, J=7.4 Hz, 3H).

Example 21

Preparation of methyl 3(R)-3-(4-chlorophenylamino)pentanoate

Methyl 3-(4-chlorophenylamino)-2-pentenoate (2.0 g, 8.3 mmol), 2-butanol (4 ml) and [RuCl(p-cymene)((R)-segphos)]Cl (7.7 mg, 0.008 mmol) were placed in a 100 ml-autoclave in a stream of nitrogen, and asymmetric hydrogenation was carried out at 70° C. under a hydrogen pressure of 3 MPa for 17 hours (conversion: 100%). The solvent was removed by evaporation under reduced pressure, and the residue was distilled under reduced pressure to give 1.75 g of the title compound (a liquid). The yield was 87%.

Chemical purity: 100%
Optical purity: 87.8% e.e.
$^1$H-NMR (CDCl$_3$, δppm): 7.10 (d, J=6.4 Hz, 2H), 6.54 (d, J=6.7 Hz, 2H), 3.72 (bs, 1H), 3.73-3.66 (m, 1H), 3.66-(s, 3H), 2.56-2.47 (m, 2H), 1.64-1.55 (m, 2H), 0.96 (t, J=7.5 Hz, 3H).

Example 22

Preparation of methyl 3(R)-3-(4-trifluoromethylphenylamino)butanoate

Methyl 3-(4-trifluoromethylphenylamino)-2-butenoate (111 g, 428 mmol), 2-butanol (220 ml) and [RuCl(p-cymene)((R)-segphos)]Cl (393 mg, 0.428 mmol) were placed in a 1L-autoclave in a stream of nitrogen, and asymmetric hydrogenation was carried out at 70° C. under a hydrogen pressure of 3 MPa for 17 hours (conversion: 100%). The solvent was removed by evaporation under reduced pressure, and the residue was distilled under reduced pressure to give 95.8 g of the title compound (a liquid). The yield was 86.4%.

Chemical purity: 100%
Optical purity: 87.4% e.e.
$^1$H-NMR (CDCl$_3$, δppm): 7.40 (d, J=8.8 Hz, 2H), 6.62 (d, J=8.6 Hz, 2H), 4.17 (bs, 1H), 4.01-3.95 (m, 1H), 3.69 (s, 3H), 2.62 (dd, J=5.3 Hz, 6.1 Hz, 1H), 2.48 (dd, J=6.6 Hz, 15.2 Hz, 1H), 1.30 (t, J=6.4 Hz, 3H).

Example 23

Preparation of methyl 3-(3,5-dichlorophenylamino)-2-pentenoate

In a 300 mL-flask were placed 3,5-dichloroaniline (25.0 g, 154 mmol), methyl 3-oxopentanoate (22.1 g, 170 mmol) and toluene (160 mL). To this solution was added p-toluenesulphonic acid monohydrate (0.59 g, 3.1 mmol), and the resulting mixture was heated in a bath kept at 100° C. under a reduced pressure of 21 kPa for 3 hours, while the water generated was taken out of the reaction system by using a Dean-Stark trap under reflux. p-Toluenesulphonic acid monohydrate (0.59 g, 3.1 mmol) was then added, and reflux was continued for 1 hour. The heating was then discontinued, nitrogen leaked in, and the reaction mixture cooled. After distillation of the solvent under reduced pressure, the residue was distilled under reduced pressure to give 27.4 g of the title compound. The yield was 64.8%.

$^1$H-NMR (500 MHz. CDCl$_3$, δppm): 10.35 (bs, 1H), 7.13 (t, J=1.8 Hz, 1H), 6.98 (d, J=1.8 Hz, 2H), 4.83 (s, 1H), 3.69 (s, 3H), 2.37 (q, J=7.4 Hz, 2H), 1.08 (t, J=7.4 Hz, 3H).

Example 24

Preparation of methyl 3(R)-3-(3,5-dichlorophenylamino)pentanoate

Methyl 3-(3,5-dichlorophenylamino)pentenoate (2.0 g, 7.3 mmol), 2-butanol (4 ml) and [RuCl(p-cymene)((R)-segphos)]Cl (6.7 mg, 0.007 mmol) were placed in a 100 ml-autoclave in a stream of nitrogen, and asymmetric hydrogenation was carried out at 80° C. under a hydrogen pressure of 3 MPa for 16 hours (conversion: 100%). The solvent was removed by evaporation under reduced pressure, and the residue was distilled under reduced pressure to give 1.72 g of the title compound (a liquid). The yield was 85%.

Chemical purity: 100%
Optical purity: 88.4% e.e.
$^1$H-NMR (500 MHz, CDCl$_3$, δppm): 6.65 (t, J=1.8 Hz, 1H), 6.47 (d, J=1.8 Hz, 2H), 3.98 (bs, 1H), 3.69-3.64 (m, 1H), 3.67 (s, 3H), 2.53 (dd, J=1.3 Hz, 5.9 Hz, 2H), 1.66-1.54 (m, 2H), 0.96 (t, J=7.4 Hz, 3H).

Industrial Applicability

One of the features of the production method of the present invention is to carry out the asymmetric hydrogenation of enaminoesters without protecting the secondary amino group with a protective group. This brings about the effect of making it possible to produce the desired optically active tetrahydroquinolines via short steps without steps of introduction and removal of the protective group, and optically active tetrahydroquinolines with high optical purity.

Another feature of the production method of the present invention is to carry out the reactions without protecting the secondary amino group of enaminoesters with a protective group. This brings about the effect of making it possible to produce the desired optically active β-amino acid derivatives via short steps without steps of introduction and removal of the protective group.

The invention claimed is:

1. A method for producing an optically active β-amino acid of formula (5a),

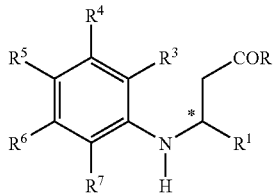

(5a)

wherein * shows an asymmetric carbon atom and R is $OR^2$ ($R^2$ is a hydrocarbon group or a substituted hydrocarbon group) or an amino group, $R^1$ is a hydrocarbon group, a substituted hydrocarbon group or $COOR^9$ ($R^9$ is a hydrocarbon group or a substituted hydrocarbon group); $R^3$ to $R^7$ are each independently a hydrogen atom, a hydrocarbon group, a halogen atom, a halogenated hydrocarbon group, a substituted hydrocarbon group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an acyl group, an acyloxy group, an alkoxycarbonyl group, an aryloxycarbonyl group, an aralkyloxycarbonyl group, an alkylenedioxy group, a hydroxyl group, a nitro group, an amino group or a substituted amino group; $R^3$ and $R^4$, $R^4$ and $R^5$, $R^5$ and $R^6$, or $R^6$ and $R^7$, taken together, may form a fused ring, with the proviso that either $R^3$ or $R^7$ is a hydrogen atom, which method comprises subjecting an enaminoester of formula (4a),

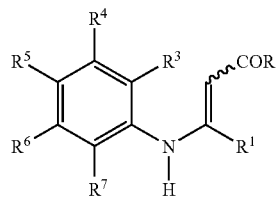

(4a)

wherein R, $R^1$ and $R^3$ to $R^7$ have the same meanings as mentioned above to an asymmetric hydrogenation.

* * * * *

UNITED STATES PATENT AND TRADEMARK OFFICE
CERTIFICATE OF CORRECTION

PATENT NO. : 8,188,307 B2  
APPLICATION NO. : 12/550948  
DATED : May 29, 2012  
INVENTOR(S) : Takashi Moroi et al.

Page 1 of 1

It is certified that error appears in the above-identified patent and that said Letters Patent is hereby corrected as shown below:

Title Page should read:

Related U.S. Application Data

Item (62)   Division of application No. 10/545,899, filed on Aug. 17, 2005, now Pat. No. 7,601,842.

Column 1, lines 7-13 should read:

This is a Divisional of U.S. application Ser. No. 10/545,899 (issued as U.S. Pat. No. 7,601,842) filed Aug. 17, 2005, which is a 371 application of PCT/JP2004/001757 filed February 17, 2004, which claims benefit of Japanese Patent Application 2003-040351 filed Feb. 18, 2003. The entire disclosures of the prior applications, application Ser. No. 10/545,899, PCT/JP2004/001757 and Japanese Patent Application 2003-040351, are hereby incorporated by reference.

Signed and Sealed this  
Eleventh Day of December, 2012

David J. Kappos  
*Director of the United States Patent and Trademark Office*